United States Patent
Walsh et al.

(10) Patent No.: US 10,604,534 B2
(45) Date of Patent: Mar. 31, 2020

(54) C5-C6-OXACYCLIC FUSED IMINOTHIADIAZINE DIOXIDE COMPOUNDS BEARING AN ETHER LINKER AS BACE INHIBITORS, COMPOSITIONS, AND THEIR USE

(71) Applicant: Merck Sharp & Dohme Corp., Rahway, NJ (US)

(72) Inventors: Shawn P. Walsh, Bridgewater, NJ (US); Jared N. Cumming, Winchester, MA (US); Xing Dai, Short Hills, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/076,441

(22) PCT Filed: Feb. 6, 2017

(86) PCT No.: PCT/US2017/016636
§ 371 (c)(1),
(2) Date: Aug. 8, 2018

(87) PCT Pub. No.: WO2017/139210
PCT Pub. Date: Aug. 17, 2017

(65) Prior Publication Data
US 2019/0040081 A1   Feb. 7, 2019

Related U.S. Application Data

(60) Provisional application No. 62/293,957, filed on Feb. 11, 2016.

(51) Int. Cl.
C07D 513/04 (2006.01)
A61P 25/28 (2006.01)

(52) U.S. Cl.
CPC ............ C07D 513/04 (2013.01); A61P 25/28 (2018.01)

(58) Field of Classification Search
CPC .................................................. C07D 513/04
USPC ..................................................... 514/222.8
See application file for complete search history.

(56) References Cited

U.S. PATENT DOCUMENTS

| | | |
|---|---|---|
| 7,763,609 B2 | 7/2010 | Zhu et al. |
| 8,183,252 B2 | 5/2012 | Zhu et al. |
| 8,691,831 B2 | 4/2014 | Zhu et al. |
| 8,691,833 B2 | 4/2014 | Zhu et al. |
| 8,729,071 B2 | 5/2014 | Scott et al. |
| 8,829,036 B2 | 9/2014 | Zhu et al. |
| 8,940,748 B2 | 1/2015 | Scott et al. |
| 9,029,362 B2 | 5/2015 | Scott et al. |
| 9,221,839 B2 | 12/2015 | Cumming et al. |
| 9,365,589 B2 | 6/2016 | Cumming et al. |
| 9,428,475 B2 | 8/2016 | Scott et al. |
| 9,475,785 B2 | 10/2016 | Scott et al. |
| 2014/0023668 A1 | 1/2014 | Cumming et al. |
| 2014/0206675 A1 | 7/2014 | Scott et al. |
| 2016/0367563 A1 | 12/2016 | Scott et al. |
| 2017/0362248 A1 | 12/2017 | Dai et al. |

OTHER PUBLICATIONS

International Search Report for PCT/US2017/016636 dated Apr. 17, 2017, 8 pages.

*Primary Examiner* — Kahsay Habte
(74) *Attorney, Agent, or Firm* — Keith D. MacMillan; Catherine D. Ficth

(57) ABSTRACT

In its many embodiments, the present invention provides certain C5-C6-oxacyclic fused iminothiadiazine dioxide compounds bearing an ether linker, including compounds Formula (I): or a tautomer thereof, and pharmaceutically acceptable salts of said compounds and said tautomers, wherein $R^N$, $R^1$, $R^2$, $R^4$, ring A, ring C, and m are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

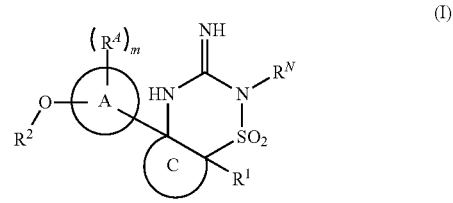

(I)

11 Claims, No Drawings

C5-C6-OXACYCLIC FUSED IMINOTHIADIAZINE DIOXIDE COMPOUNDS BEARING AN ETHER LINKER AS BACE INHIBITORS, COMPOSITIONS, AND THEIR USE

FIELD OF THE INVENTION

This invention provides certain C5-C6-oxacyclic fused iminothiadiazine dioxide compounds bearing an ether linker, and compositions comprising these compounds, as inhibitors of BACE, which may be useful for treating or preventing pathologies related thereto, including, but not limited to, Alzheimer's disease.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of A3, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, certain groups have suggested the potential of BACE inhibition may be useful for traumatic brain injury. (Loane et al., "Amyloid precursor protein secretases as therapeutic targets for traumatic brain injury", Nature Medicine, 15, 377-379 (2009); Yu, et al., "Lithium reduces BACE1 overexpression, β amyloid accumulation, and spatial learning deficits in mice with traumatic brain injury", J Neurotrauma, 2012 September; 29(13): 2342-51; Tran, et al., "Controlled cortical impact traumatic brain injury in 3xTg-AD mice causes acute intra-axonal amyloid-β accumulation and independently accelerates the development of tau abnormalities", J Neurosci. 2011 Jun. 29; 31(26):9513-25). Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

WO2012138734 discloses certain C5-C6-oxacyclic fused imino thiadiazine dioxide compounds as BACE inhibitors. There remains a need in the art, however, for potent BACE inhibitors. The compounds of the present invention address this need.

SUMMARY OF THE INVENTION

The present invention provides certain C5-C6-oxacyclic fused iminothiadiazine dioxide compounds bearing an ether linker, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

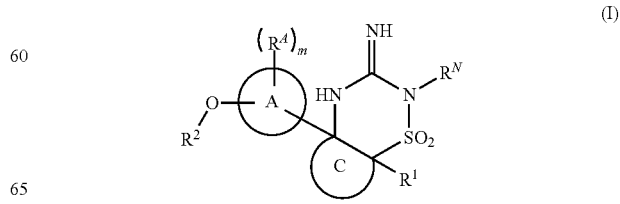

or a tautomer thereof having the structural Formula (I'):

$$\text{(I')}$$

or pharmaceutically acceptable salt thereof, wherein:
ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group,
  wherein $R^{C1}$ and $R^{C2}$ are each independently selected from the group consisting of H, halogen, —C(O)O—($C_1$-$C_6$-alkyl), alkyl, cycloalkyl, -alkyl-cycloalkyl, -heterocycloalkyl, -alkyl-heterocycloalkyl, aryl, -alkyl-aryl, heteroaryl, and -alkyl-heteroaryl,
    wherein each said alkyl, cycloalkyl, heterocycloalkyl, aryl, and heteroaryl of $R^{C1}$ and $R^{C2}$ are optionally substituted with one or more $R^3$, and
    wherein 1 to 2 non-adjacent, non-terminal carbon atoms in each said alkyl of $R^{C1}$ and $R^{C2}$ are optionally independently replaced with —O—, —NH—, —N($C_1$-$C_6$-alkyl)-, —S—, —S(O)—, or —S(O)$_2$—,
  or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms, wherein 1 of said carbon atoms may be replaced with —O—, —NH—, —N($C_1$-$C_6$-alkyl)-, —N($C_1$-$C_6$-haloalkyl)-, —S—, —S(O)—, or —S(O)$_2$—, and
    wherein 1 to 2 of the carbon atoms of said spirocyclic ring may be optionally independently substituted with 1 to 2 fluorine, $C_1$-$C_6$-alkyl, $C_1$-$C_6$-haloalkyl, or —CH$_2$O—($C_1$-$C_6$-alkyl);
$R^N$ is selected from the group consisting of H, alkyl, cycloalkyl, and -alkyl-cycloalkyl, wherein each said alkyl and cycloalkyl are optionally substituted with one or more fluorine, and
  wherein 1 to 2 non-adjacent, non-terminal carbon atoms in each said alkyl are optionally independently replaced with —O—, —NH—, —N($C_1$-$C_6$-alkyl)-, —S—, —S(O)—, or —S(O)$_2$—;
$R^1$ is selected from the group consisting of H, halogen, and alkyl,
  wherein said alkyl is optionally substituted with one or more fluorine, and
  wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;
ring A is selected from the group consisting of aryl and heteroaryl;
m is 0 or more, provided that the value of m does not exceed the number of available substitutable hydrogen atoms on ring A;
each $R^A$ (when present) is independently selected from the group consisting of halogen, oxo, —OH, —CN, alkyl, and cycloalkyl,
  wherein said alkyl, and cycloalkyl of $R^A$ are each optionally independently unsubstituted or substituted with one or more fluorine, and
  wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;
$R^2$ is -alkyl-cycloalkyl,
  wherein said alkyl is optionally substituted with one or more fluorine, and wherein said cycloalkyl is optionally substituted with one or two groups independently selected from $R^3$,
  or alternatively $R^2$ is a moiety having the formula wherein ring B is selected from the group consisting of aryl, heteroaryl, cycloalkyl, and heterocycloalkyl;
p is 0 or more, provided that the value of p does not exceed the number of available substitutable hydrogen atoms on ring B; and
each $R^B$ (when present) is independently selected from the group consisting of halogen, oxo, —OH, —CN, —SF$_5$, —OSF$_5$, —OR$^{2B}$, —SR$^{2B}$, alkyl, alkenyl, alkynyl, cycloalkyl, -alkyl-cycloalkyl, heterocycloalkyl, -alkyl-heterocycloalkyl, aryl, and heteroaryl,
  wherein each said alkyl, alkenyl, alkynyl, cycloalkyl, heterocycloalkyl, aryl, and heteroaryl of $R^B$ are each optionally independently unsubstituted or substituted with one or more groups independently selected from $R^3$, and wherein 1 to 2 non-adjacent, non-terminal carbon atoms in each said alkyl are optionally independently replaced with —O—, —NH—, —N($C_1$-$C_6$-alkyl)-, —S—, —S(O)—, or —S(O)$_2$—;
each $R^{2B}$ is independently selected from the group consisting of H, alkyl, alkenyl, alkynyl, cycloalkyl, -alkyl-cycloalkyl, heterocycloalkyl, and -alkyl-heterocycloalkyl,
  wherein each said alkyl, alkenyl, alkynyl, cycloalkyl, and heterocycloalkyl of $R^{2B}$ is unsubstituted or optionally substituted with one or more fluorine, and
  wherein 1 to 2 non-adjacent, non-terminal carbon atoms in each said alkyl are optionally independently replaced with —O—, —NH—, —N(alkyl)-, —S—, —S(O)—, or —S(O)$_2$—; and
each $R^3$ (when present) is independently selected from the group consisting of halogen, —OH, —CN, $C_1$-$C_6$-alkyl, $C_2$-$C_6$-alkenyl, $C_2$-$C_6$-alkynyl, —($C_1$-$C_6$-alkyl)-OH, —O—($C_1$-$C_6$-alkyl), $C_3$-$C_6$-cycloalkyl, —($C_1$-$C_6$-alkyl)-($C_3$-$C_6$-cycloalkyl), —O—($C_3$-$C_6$-cycloalkyl), —O—($C_1$-$C_6$-alkyl)-($C_3$-$C_6$-cycloalkyl), $C_4$-$C_6$-heterocycloalkyl, —($C_1$-$C_6$-alkyl)-($C_4$-$C_6$-heterocycloalkyl), —O—($C_4$-$C_6$-heterocycloalkyl), —O—($C_1$-$C_6$-alkyl)-($C_4$-$C_6$-heterocycloalkyl), —NH$_2$, —NH—($C_1$-$C_6$-alkyl), and —N—($C_1$-$C_6$-alkyl)$_2$,
  wherein each said $C_1$-$C_6$-alkyl, $C_3$-$C_6$-cycloalkyl, and $C_4$-$C_6$-heterocycloalkyl are optionally substituted with one or more halogen,
  and wherein 1 to 2 non-adjacent, non-terminal carbon atoms in each said $C_1$-$C_6$-alkyl are optionally independently replaced with —O—, —NH—, —N—($C_1$-$C_6$-alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I), (I'), (IA), or (IA'). In each of the embodiments described herein, each variable is selected independently of the other unless otherwise noted.

In one embodiment, the compounds of the invention have the structural Formula (IA):

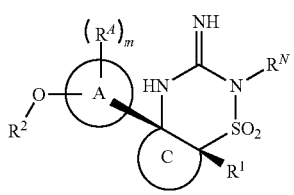

(IA)

or a tautomer thereof having the structural Formula (IA'):

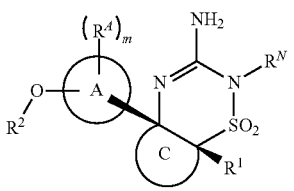

(IA')

or pharmaceutically acceptable salt thereof, wherein each variable is as described in Formula (I).

In one embodiment, in each of Formulas (I), (I'), (IA), and (IA'):
ring C is selected from the group consisting of

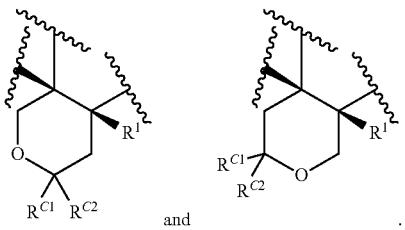

and

In one embodiment, in each of Formulas (I), (I'), (IA), and (IA'):
ring C is

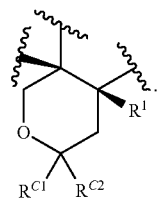

The following alternative embodiments of $R^{C1}$ and $R^{C2}$ are contemplated in combination with any of the embodiments described above.

In one embodiment, in each of Formulas (I), (I'), (IA), and (IA'):
$R^{C1}$ and $R^{C2}$ are each independently selected from the group consisting of H, —$CO_2CH_3$, —$CO_2CH_2CH_3$, —$CO_2CH(CH_3)_3$, methyl, ethyl, propyl, butyl, cyclopropyl, —$CH_2$-cyclopropyl, cyclobutyl, —$CH_2$-cyclobutyl, —$CH_2OH$, —$CH_2OCH_3$, —$CH_2OCH_2CH_3$, phenyl, pyridyl, pyrimidinyl, pyrazinyl, oxazoyl, isooxazoyl, thiazoyl, isothiazolyl, pyrazolyl, benzodioxolyl, benzofuranyl, dihydrobenzofuranyl, benzyl, —$CH_2$-pyridyl, —$CH_2$-pyrimidinyl, and —$CH_2$-pyrazinyl,
wherein each said methyl, ethyl, propyl, butyl, cyclopropyl, —$CH_2$-cyclopropyl, cyclobutyl, —$CH_2$-cyclobutyl, —$CH_2OCH_3$, and —$CH_2OCH_2CH_3$ of $R^{C1}$ and $R^{C2}$ is optionally substituted with one or more fluorine, and
wherein each said phenyl, pyridyl, pyrimidinyl, pyrazinyl, oxazoyl, isoxazoyl, thiazoyl, isothiazolyl, pyrazolyl, benzodioxolyl, benzofuranyl, dihydrobenzofuranyl, benzyl, —$CH_2$-pyridyl, —$CH_2$-pyrimidinyl, and —$CH_2$-pyrazinyl of $R^{C1}$ and $R^{C2}$ is unsubstituted or substituted with one or more groups independently selected from the group consisting of fluorine, chlorine, bromine, methyl, ethyl, propyl, cyclopropyl, —$OCH_3$, —$OCH_2CH_3$, and —O-cyclopropyl,
wherein each said methyl, ethyl, propyl, cyclopropyl, —$OCH_3$, —$OCH_2CH_3$, and —O-cyclopropyl is each optionally substituted with from 1 to 3 fluorine.

In one embodiment, in each of Formulas (I), (I'), (IA), and (IA'):
$R^{C1}$ and $R^{C2}$ are each independently selected from the group consisting of H, —$CO_2CH_3$, methyl, ethyl, cyclopropyl, —$CH_2OH$, —$CH_2OCH_3$, phenyl, pyridyl, pyrimidinyl, oxazoyl, isoxazoyl, and pyrazolyl, wherein each said methyl, ethyl, cyclopropyl, and —CH$_2$OCH$_3$, of R$^{C1}$ and R$^{C2}$ is optionally substituted with one or more fluorine, and wherein each said phenyl, pyridyl, pyrimidinyl, oxazoyl, isoxazoyl, and pyrazolyl of R$^{C1}$ and R$^{C2}$ is unsubstituted or substituted with one or more groups independently selected from the group consisting of fluorine, methyl, ethyl, cyclopropyl, and —OCH$_3$, wherein each said methyl, ethyl, cyclopropyl, and —OCH$_3$ is each optionally substituted with from 1 to 3 fluorine.

In one embodiment, in each of Formulas (I), (I'), (IA), and (IA'):

R$^{C1}$ and R$^{C2}$ are each independently selected from the group consisting of H, —CO$_2$CH$_3$, methyl, —CHF$_2$, cyclopropyl, —CH$_2$OCH$_3$, phenyl, and isoxazoyl, wherein each said phenyl and isoxazoyl of R$^{C1}$ and R$^{C2}$ is unsubstituted or substituted with one or more groups independently selected from the group consisting of fluorine and methyl.

In one embodiment, in each of Formulas (I), (I'), (IA), and (IA'):

R$^{C1}$ and R$^{C2}$ are each independently selected from the group consisting of H, methyl, and —CH$_2$OCH$_3$.

In one embodiment, in each of Formulas (I), (I'), (IA), and (IA'):

R$^{C2}$ is selected from the group consisting of H and methyl.

In one embodiment, in each of Formulas (I), (I'), (IA), and (IA'):

R$^{C2}$ is H.

In one embodiment, in each of Formulas (I), (I'), (IA), and (IA'):

R$^{C1}$ is selected from the group consisting of H, —CO$_2$CH$_3$, methyl, ethyl, cyclopropyl, —CH$_2$OH, —CH$_2$OCH$_3$, phenyl, pyridyl, pyrimidinyl, oxazoyl, isoxazoyl, and pyrazolyl, wherein each said methyl, ethyl, cyclopropyl, and —CH$_2$OCH$_3$, of R$^{C1}$ is optionally substituted with one or more fluorine, and wherein each said phenyl, pyridyl, pyrimidinyl, oxazoyl, isoxazoyl, and pyrazolyl of R$^{C1}$ is unsubstituted or substituted with one or more groups independently selected from the group consisting of fluorine, methyl, ethyl, cyclopropyl, and —OCH$_3$, wherein each said methyl, ethyl, cyclopropyl, and —OCH$_3$ is each optionally substituted with from 1 to 3 fluorine; and R$^{C2}$ is selected from the group consisting of H and methyl.

In one embodiment, in each of Formulas (I), (I'), (IA), and (IA'):

R$^{C1}$ is selected from the group consisting of H, —CO$_2$CH$_3$, methyl, —CHF$_2$, cyclopropyl, —CH$_2$OCH$_3$, phenyl, and isoxazoyl, wherein each said phenyl and isoxazoyl of R$^{C1}$ is unsubstituted or substituted with one or more groups independently selected from the group consisting of fluorine and methyl; and R$^{C2}$ is selected from the group consisting of H and methyl.

In one embodiment, in each of Formulas (I), (I'), (IA), and (IA'):

R$^{C1}$ is selected from the group consisting of H, methyl, and —CH$_2$OCH$_3$; and R$^{C2}$ is H.

In one embodiment, in each of Formulas (I), (I'), (IA), and (IA'):

ring C is

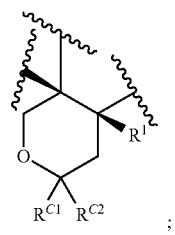

and

R$^{C1}$ and R$^{C2}$ are each independently selected from the group consisting of H, —CO$_2$CH$_3$, methyl, —CHF$_2$, cyclopropyl, —CH$_2$OCH$_3$, phenyl, and isoxazoyl, wherein each said phenyl and isoxazoyl of R$^{C1}$ and R$^{C2}$ is unsubstituted or substituted with one or more groups independently selected from the group consisting of fluorine and methyl.

In one embodiment, in each of Formulas (I), (I'), (IA), and (IA'):

ring C is

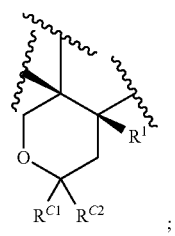

R$^{C1}$ is selected from the group consisting of H, —CO$_2$CH$_3$, methyl, —CHF$_2$, cyclopropyl, —CH$_2$OCH$_3$, phenyl, and isoxazoyl, wherein each said phenyl and isoxazoyl of R$^{C1}$ is unsubstituted or substituted with one or more groups independently selected from the group consisting of fluorine and methyl; and R$^{C2}$ is selected from the group consisting of H and methyl.

In one embodiment, in each of Formulas (I), (I'), (IA), and (IA'):

ring C is

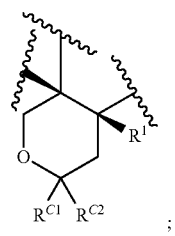

R$^{C1}$ is selected from the group consisting of H, methyl, and —CH$_2$OCH$_3$; and R$^{C2}$ is selected from the group consisting of H and methyl.

In one embodiment, in each of Formulas (I), (I'), (IA), and (IA'):
ring C is

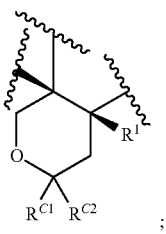

$R^{C1}$ is selected from the group consisting of H, methyl, and —CH$_2$OCH$_3$; and
$R^{C2}$ is H.

In one embodiment, in each of Formulas (I), (I'), (IA), and (IA'):
ring C is

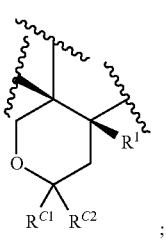

and
$R^{C1}$ and $R^{C2}$ taken together with the carbon to which they are attached form a spirocyclic ring selected from the group consisting of spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl,
  wherein 1 to 2 of the carbon atoms of said spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl is unsubstituted or substituted with 1 to 2 groups independently selected from the group consisting of fluorine, methyl, cyclopropyl, and —OCH$_3$,
  wherein each said methyl, cyclopropyl, and —OCH$_3$ is each optionally substituted with from 1 to 3 fluorine,
  and wherein each of the nitrogen atoms of said spiroazetidinyl, spiropyrrolidinyl, and spiropiperidinyl is unsubstituted or substituted with methyl, ethyl, propyl, and —CH$_2$CF$_3$.

The following alternative embodiments of $R^N$ are contemplated in combination with any of the embodiments described above.

In one embodiment, in each of Formulas (I), (I'), (IA), and (IA'):
$R^N$ is selected from the group consisting of H, methyl, ethyl, cyclopropyl, —CH$_2$-cyclopropyl, and —CH$_2$CH$_2$OCH$_3$,
  wherein each said methyl, ethyl, cyclopropyl, —CH$_2$-cyclopropyl, and —CH$_2$CH$_2$OCH$_3$ is each optionally substituted with from 1 to 3 fluorine.

In one embodiment, in each of Formulas (I), (I'), (IA), and (IA'):
$R^N$ is selected from the group consisting of H and methyl.

In one embodiment, in each of Formulas (I), (I'), (IA), and (IA'):
$R^N$ is methyl.

The following alternative embodiments of $R^1$ are contemplated in combination with any of the embodiments described above.

In one embodiment, in each of Formulas (I), (I'), (IA), and (IA'):
$R^1$ is selected from the group consisting of H, fluoro, methyl, and —CH$_2$OCH$_3$.

In one embodiment, in each of Formulas (I), (I'), (IA), and (IA'):
$R^1$ is H.

In one embodiment, in each of Formulas (I), (I'), (IA), and (IA'):
$R^N$ is selected from the group consisting of H, methyl, ethyl, cyclopropyl, —CH$_2$-cyclopropyl, and —CH$_2$CH$_2$OCH$_3$,
  wherein each said methyl, ethyl, cyclopropyl, —CH$_2$-cyclopropyl, and —CH$_2$CH$_2$OCH$_3$ is each optionally substituted with from 1 to 3 fluorine; and
  $R^1$ is selected from the group consisting of H, fluoro, methyl, and —CH$_2$OCH$_3$.

In one embodiment, in each of Formulas (I), (I'), (IA), and (IA'):
$R^N$ is selected from the group consisting of H and methyl; and
$R^1$ is H.

In one embodiment, in each of Formulas (I), (I'), (IA), and (IA'):
$R^N$ is methyl; and
$R^1$ is H.

The following alternative embodiments of ring A, m, $R^4$, and $R^2$ are contemplated in combination with any of the embodiments described above.

In one embodiment, in each of Formulas (I), (I'), (IA), and (IA'):
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, or 3; provided that the value of m does not exceed the number of available substitutable hydrogen atoms on ring A; and
each $R^4$ (when present) is independently selected from the group consisting of fluoro, chloro, bromo, —CN, methyl, ethyl, cyclopropyl, —CH$_2$OCH$_3$, —CF$_3$, —CHF$_2$, —CH$_2$F, —OCH$_3$, —OCF$_3$, and —OCHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3, provided that the value of m does not exceed the number of available substitutable hydrogen atoms on ring A.

In one embodiment, in each of Formulas (I), (I'), (IA), and (IA'):
ring A is selected from the group consisting of phenyl, pyridinyl, and thienyl;
m is 0, 1, 2, or 3; provided that the value of m does not exceed the number of available substitutable hydrogen atoms on ring A; and
each $R^4$ (when present) is independently selected from the group consisting of fluoro, chloro, methyl, and —CHF$_2$.

In an alternative of the immediately preceeding embodiment, m is 0. In another alternative of the immediately preceding embodiment, m is 1. In another alternative of the immediately preceding embodiment, m is 2. In another alternative of the immediately preceding embodiment, m is 3, provided that the value of m does not exceed the number of available substitutable hydrogen atoms on ring A.

In one embodiment, in each of Formulas (I), (I'), (IA), and (IA'):
ring A is selected from the group consisting of phenyl and pyridinyl;
m is 0, 1, 2, or 3; and
each $R^A$ (when present) is fluoro.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
ring A is phenyl;
m is 0, 1, or 2; and
each $R^A$ (when present) is fluoro.

In an alternative of the immediately preceding embodiment, m is 0. In another alternative of the immediately preceding embodiment, m is 1. In another alternative of the immediately preceding embodiment, m is 2.

In one embodiment, in each of Formulas (I), (I'), (IA), and (IA'):
$R^2$ is —($C_1$-$C_3$-alkyl)-($C_3$-$C_6$-cycloalkyl),
wherein said $C_1$-$C_3$-alkyl is optionally substituted with one or more fluorine, provided that the number of fluorine atoms does not exceed the number of available substitutable hydrogen atoms on said $C_1$-$C_3$-alkyl group, and
wherein said $C_3$-$C_6$-cycloalkyl is optionally substituted with one or two groups independently selected from the group consisting of fluoro, chloro, —CN, methyl, ethyl, —$CH_2F$, —$CHF_2$, —$CF_3$, —$CF_2CH_3$, —$CH_2OCH_3$,

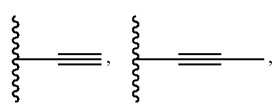

—$CH_2OH$, —OMe, —$OCH_2F$, —$OCHF_2$, —$OCF_3$, —$NH_2$, —$NHCH_3$, —$N(CH_3)_2$, —$CH_2NH_2$, —$CH_2NHCH_3$, and —$CH_2N(CH_3)$.

In one embodiment, in each of Formulas (I), (I'), (IA), and (IA'):
$R^2$ is selected from the group consisting of —$CH_2$-cyclopropyl, —$CF_2$-cyclopropyl, —$CH_2CH_2$-cyclopropyl, —$CH_2$-cyclobutyl, —$CH_2CH_2$-cyclobutyl, —$CH_2$-cyclopentyl, —$CH_2$-cyclohexyl, and —$CH_2$-([1.1.1]bicyclopentane),
wherein each said cyclopropyl, cyclobutyl, cyclopentyl, cyclohexyl, and [1.1.1]-bicyclopentane is optionally substituted with 1 to 2 substituents independently selected from the group consisting of fluoro, chloro, —CN, methyl, ethyl, —$CH_2F$, —$CHF_2$, —$CF_2CH_3$, —$CH_2OCH_3$,

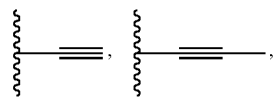

—$CH_2OH$, —OMe, —$NH_2$, —$NHCH_3$, —$N(CH_3)_2$, —$CH_2NH_2$, —$CH_2NHCH_3$, and —$CH_2N(CH_3)$.

In one embodiment, in each of Formulas (I), (I'), (IA), and (IA'):
$R^2$ is selected from the group consisting of —$CH_2$-cyclopropyl, —$CH_2$-cyclobutyl,

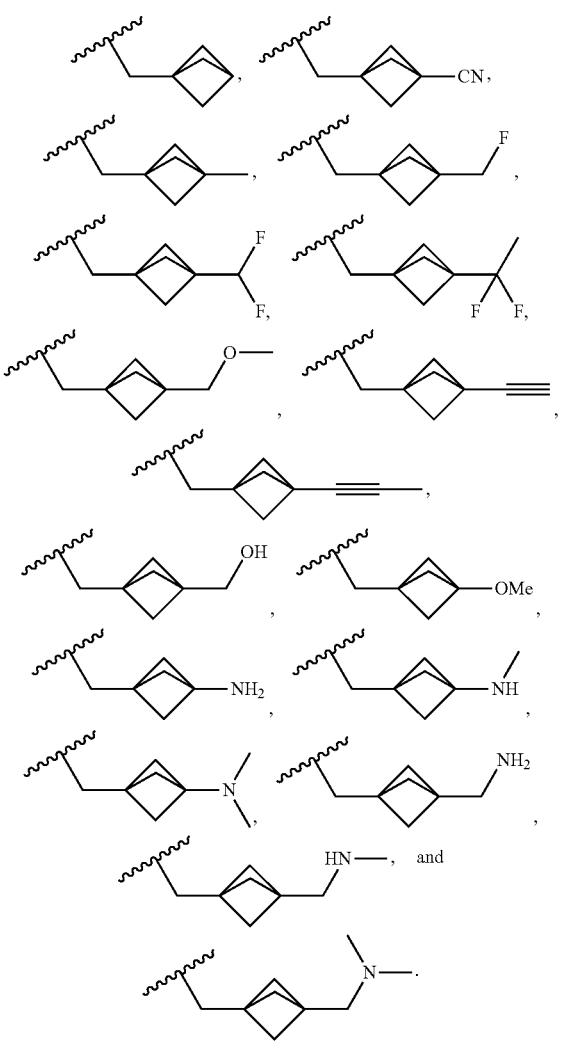

In one embodiment, in each of Formulas (I), (I'), (IA), and (IA'):
$R^2$ is selected from the group consisting of —$CH_2$-cyclopropyl and

In one embodiment, in each of Formulas (I), (I'), (IA), and (IA'):
ring A is selected from the group consisting of phenyl and pyridinyl;
m is 0, 1, 2, or 3;
each $R^A$ (when present) is fluoro; and
$R^2$ is selected from the group consisting of —CH$_2$-cyclopropyl, —CF$_2$-cyclopropyl, —CH$_2$CH$_2$-cyclopropyl, —CH$_2$-cyclobutyl, —CH$_2$CH$_2$-cyclobutyl, —CH$_2$-cyclopentyl, —CH$_2$-cyclohexyl, —CH$_2$-([1.1.1]-bicyclopentane), wherein each said cyclopropyl, cyclobutyl, cyclopentyl, cyclohexyl, and [1.1.1]-bicyclopentane is optionally substituted with 1 to 2 substituents independently selected from the group consisting of fluoro, chloro, —CN, methyl, ethyl, —CH$_2$F, —CHF$_2$, —CF$_2$CH$_3$, —CH$_2$OCH$_3$,

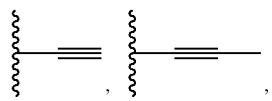

—CH$_2$OH, —OMe, —NH$_2$, —NHCH$_3$, —N(CH$_3$)$_2$, —CH$_2$NH$_2$, —CH$_2$NHCH$_3$, and —CH$_2$N(CH$_3$).

In one embodiment, in each of Formulas (I), (I'), (IA), and (IA'):
ring A is selected from the group consisting of phenyl and pyridinyl;
m is 0, 1, 2, or 3;
each $R^A$ (when present) is fluoro; and
$R^2$ is selected from the group consisting of —CH$_2$-cyclopropyl, —CH$_2$-cyclobutyl,

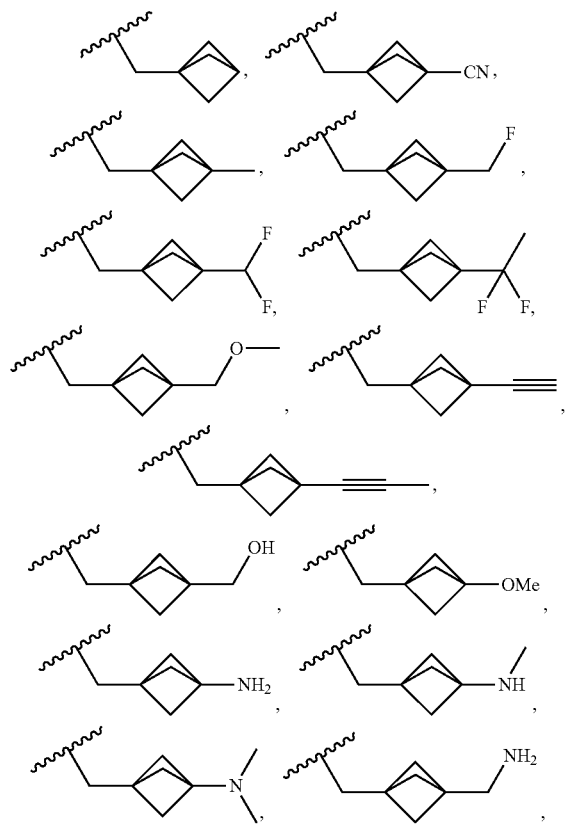

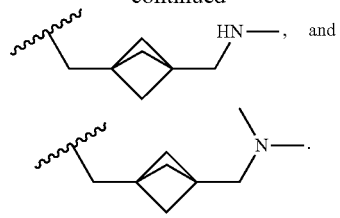

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
ring A is selected from the group consisting of phenyl and pyridinyl;
m is 0, 1, 2, or 3;
each $R^A$ (when present) is fluoro; and
$R^2$ is selected from the group consisting of —CH$_2$-cyclopropyl and

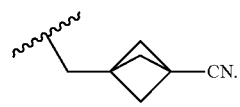

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
ring A is phenyl;
m is 0, 1, or 2;
each $R^A$ (when present) is fluoro; and
$R^2$ is selected from the group consisting of —CH$_2$-cyclopropyl and

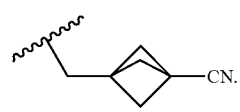 [SMILES: *CC12CC(C#N)(C1)C2]

In an alternative of the immediately preceding embodiment, m is 0. In another alternative of the immediately preceding embodiment, m is 1. In another alternative of the immediately preceding embodiment, m is 2.

In some embodiments, in each of Formulas (I), (I'), (IA), and (IA'):
$R^2$ is a moiety having the formula

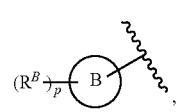

wherein ring B, p, and $R^B$ are each as defined in Formula (I).

In these embodiments, the moiety

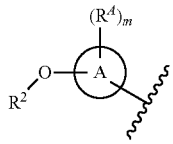

has the form

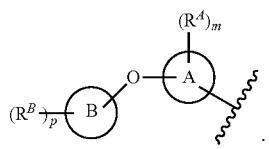

In one embodiment, in each of Formulas (I), (I'), (IA), and (IA'):

R² is a moiety having the formula

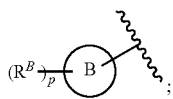

ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

p is 0, 1, 2, or 3, provided that the value of p does not exceed the number of available substitutable hydrogen atoms on ring B; and each R$^B$ group (when present) is independently selected from the group consisting of halogen, oxo, —OH, —CN, —OCH₃, —OCH₂CH₃, —O-cyclopropyl, —O—CH₂-cyclopropyl, —OCH₂—C≡C—H, —OCH₂—C≡C—CH₃, methyl, ethyl, propyl, cyclopropyl, —CH₂-cyclopropyl, —CH₂OCH₃, —CH₂OCH₂CH₃, —C≡CH, —C≡C—CH₃—CF₃, —CHF₂, —CH₂F, —OCF₃, —OCH₂CF₃, —OCHF₂, —OCH₂F, —OCH₂CH₂F, phenyl, pyridinyl, oxadiazolyl, isoxazolyl, oxazolyl, pyrazolyl, pyrrolyl, and triazolyl, wherein each said phenyl, pyridinyl, oxadiazolyl, isoxazolyl, oxazolyl, pyrazolyl, pyrrolyl, and triazolyl is optionally substituted with from 1 to 3 substituents independently selected from the group consisting of fluoro, chloro, —CN, methyl, —OCH₃, and —CF₃.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, provided that the value of p does not exceed the number of available substitutable hydrogen atoms on ring B.

In one embodiment, in each of Formulas (I), (I'), (IA), and (IA'):

R² is a moiety having the formula

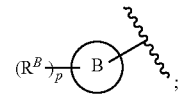

ring B is selected from the group consisting of cyclobutyl, cyclopentyl, cyclopropyl, phenyl, piperidinyl, pyrazinyl, pyrazolyl, pyridazinyl, pyridinyl, pyrimidinyl, pyrrolidinyl, tetrahydrofuranyl, tetrahydropyranyl;

p is 0, 1, 2, or 3, provided that the value of p does not exceed the number of available substitutable hydrogen atoms on ring B; and each R$^B$ group (when present) is independently selected from the group consisting of fluoro, chloro, —CN, —OCH₃, —O—CH₂-cyclopropyl, —OCH₂—C≡C—H, —OCH₂—C≡C—CH₃, methyl, ethyl, cyclopropyl, —CH₂-cyclopropyl, —CH₂OCH₃, —C≡CH, —C≡C—CH₃—CF₃, —CHF₂, —OCF₃, —OCHF₂, oxadiazolyl, isoxazolyl, oxazolyl, pyrazolyl, pyrrolyl, and triazolyl, wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, provided that the value of p does not exceed the number of available substitutable hydrogen atoms on ring B.

In one embodiment, in each of Formulas (I), (I'), (IA), and (IA'):

R² is a moiety having the formula

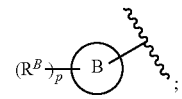

ring B is selected from the group consisting of cyclobutyl, phenyl, pyrazinyl, pyridazinyl, pyridinyl, and pyrimidinyl;

p is 0, 1, or 2; and each R$^B$ group (when present) is independently selected from the group consisting of fluoro, chloro, methyl, —CN, —OMe, —CHF₂, oxazolyl, pyrazolyl, and triazolyl.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

R² is a moiety having the formula

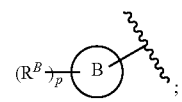

ring B is selected from the group consisting of pyrazinyl, pyridinyl, and pyrimidinyl;

p is 0, 1, or 2; and each $R^B$ group (when present) is independently selected from the group consisting of fluoro, chloro, —CN, and —OMe.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

ring A is selected from the group consisting of phenyl and pyridinyl;

m is 0, 1, 2, or 3;

each $R^A$ (when present) is fluoro;

$R^2$ is a moiety having the formula

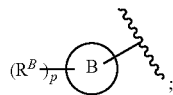

ring B is selected from the group consisting of cyclobutyl, cyclopentyl, cyclopropyl, phenyl, piperidinyl, pyrazinyl, pyrazolyl, pyridazinyl, pyridinyl, pyrimidinyl, pyrrolidinyl, tetrahydrofuranyl, tetrahydropyranyl;

p is 0, 1, 2, or 3, provided that the value of p does not exceed the number of available substitutable hydrogen atoms on ring B; and each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡CH$_3$—CF$_3$, —CHF$_2$, —OCF$_3$, —OCHF$_2$, oxadiazolyl, isoxazolyl, oxazolyl, pyrazolyl, pyrrolyl, and triazolyl, wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, provided that the value of p does not exceed the number of available substitutable hydrogen atoms on ring B.

In one embodiment, in each of Formulas (I), (I'), (IA), and (IA'):

ring A is selected from the group consisting of phenyl and pyridinyl;

m is 0, 1, 2, or 3;

each $R^A$ (when present) is fluoro;

$R^2$ is a moiety having the formula

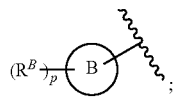

ring B is selected from the group consisting of cyclobutyl, phenyl, pyrazinyl, pyridazinyl, pyridinyl, and pyrimidinyl;

p is 0, 1, or 2; and each $R^B$ group (when present) is independently selected from the group consisting of fluoro, methyl, —CN, —OMe, —CHF$_2$, oxazolyl, pyrazolyl, and triazolyl.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

ring A is selected from the group consisting of phenyl and pyridinyl;

m is 0, 1, 2, or 3;

each $R^A$ (when present) is fluoro;

$R^2$ is a moiety having the formula

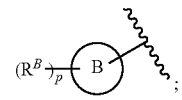

ring B is selected from the group consisting of pyrazinyl, pyridinyl, and pyrimidinyl;

p is 0, 1, or 2; and each $R^B$ group (when present) is independently selected from the group consisting of fluoro, chloro, —CN, and —OMe.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

ring A is phenyl;

m is 0, 1, or 2;

each $R^A$ (when present) is fluoro;

$R^2$ is a moiety having the formula

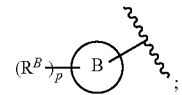

ring B is selected from the group consisting of pyrazinyl, pyridinyl, and pyrimidinyl;

p is 0, 1, or 2; and each $R^B$ group (when present) is independently selected from the group consisting of fluoro, chloro, —CN, and —OMe.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

Specific non-limiting examples of compounds of the invention are shown in the table of examples below. While only one tautomeric form of each compound is shown in the tables, it shall be understood that both tautomeric forms of the compounds are contemplated as being within the scope of the non-limiting examples.

In another embodiment, in each of Formulas (I), (I'), (IA), and (IA'), 1 to 3 carbon atoms of the compounds of the invention may be replaced with 1 to 3 silicon atoms so long as all valency requirements are satisfied.

Another embodiment provides a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H, -inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB 1 receptor inverse agonists or CB 1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset of, mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of"hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 6 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, i-propyl, n-butyl, i-butyl, and t-butyl.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

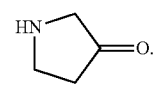

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

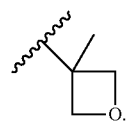

It should be noted that in hetero-atom containing ring systems of this invention, there are no hydroxyl groups on carbon atoms adjacent to a N, O or S, as well as there are no N or S groups on carbon adjacent to another heteroatom.

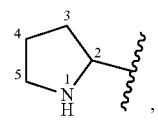 [SMILES: *C1CCCN1]

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in $-N(R^6)_2$, or a variable appears more than once in a structure presented herein, the variables can be the same or different.

The line ——, as a bond generally indicates a mixture of, or either of, the possible isomers, e.g., containing (R)- and (S)-stereochemistry. For example:

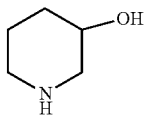

means containing both

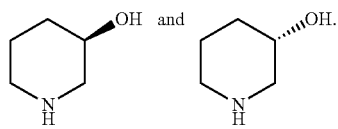

The wavy line ~~~, as used herein, indicates a point of attachment to the rest of the compound. Lines drawn into the ring systems, such as, for example:

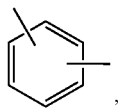

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

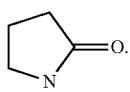

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

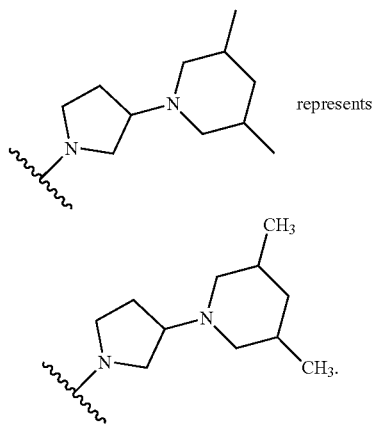

represents

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, compounds of the invention conforming to the formula:

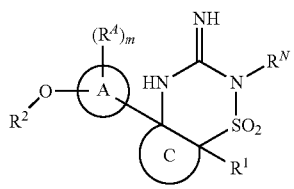

and its tautomer, which can be depicted as:

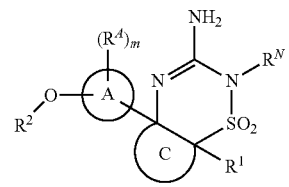

are both contemplated as being within the scope of the compounds of the invention. As noted above, while only one said tautomeric form of each example compound of the invention may be shown in the tables and appended claims, it shall be understood that both of these tautomeric forms of the compounds are contemplated as being within the scope of the non-limiting example compounds of the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:
Acetonitrile: MeCN, ACN
Aqueous: aq.
Concentrated: conc.
Dess-Martin Periiodinane: DMP
Di-tert-butyldicarbonate: Boc$_2$O
Dichloromethane: DCM
Diisopropylethylamine: DIEA or iPr$_2$NEt
Dimethylacetamide: DMA
Dimethylformamide: DMF
Dimethylsulfoxide: DMSO
4,5-bis(Diphenylphosphino)-9,9-
Electrospray: ES
Ethanol: EtOH
Ethyl: Et
Ethyl acetate: AcOEt, EtOAc, or EA
Example: Ex.
Grams: g
Hexanes: hex
High performance liquid chromatography: HPLC
Hours: h
Liquid chromatography mass Spectrometry: LCMS
Liter: L
Lithium bis(trimethylsilyl)amide: LHMDS
Methanol: MeOH
Microliters: μl or μL
Micrometers or microns: um or μm
Milligrams: mg
Milliliters: mL
Millimeters: mm
Millimoles: mmol
Micromoles: uM or μM
Minutes: min
Molar: M
n-Butyllithium: nBuLi or n-BuLi
Normal: N
Nuclear magnetic resonance spectroscopy: NMR
Petroleum ether: PE
Preparative: prep-, p-
Room temperature (ambient, about 25° C.): rt or RT
Saturated: sat.
Silica gel: SiO$_2$
Supercritical Fluid Chromatography: SFC
tert-Butoxycarbonyl: t-Boc or Boc
Temperature: temp.
Tetrahydrofuran: THF
Thin layer chromatography: TLC
Triethylamine: Et$_3$N or TEA
Trifluoroacetic acid: TFA
Trimethylsilyl: TMS-

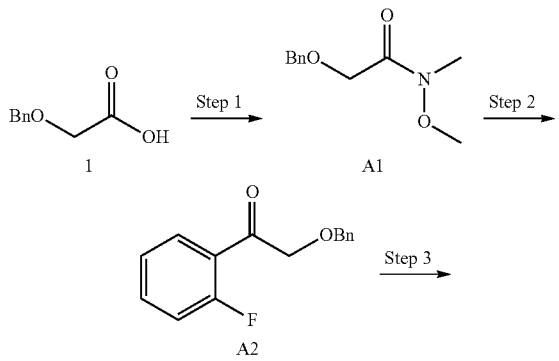

Method A

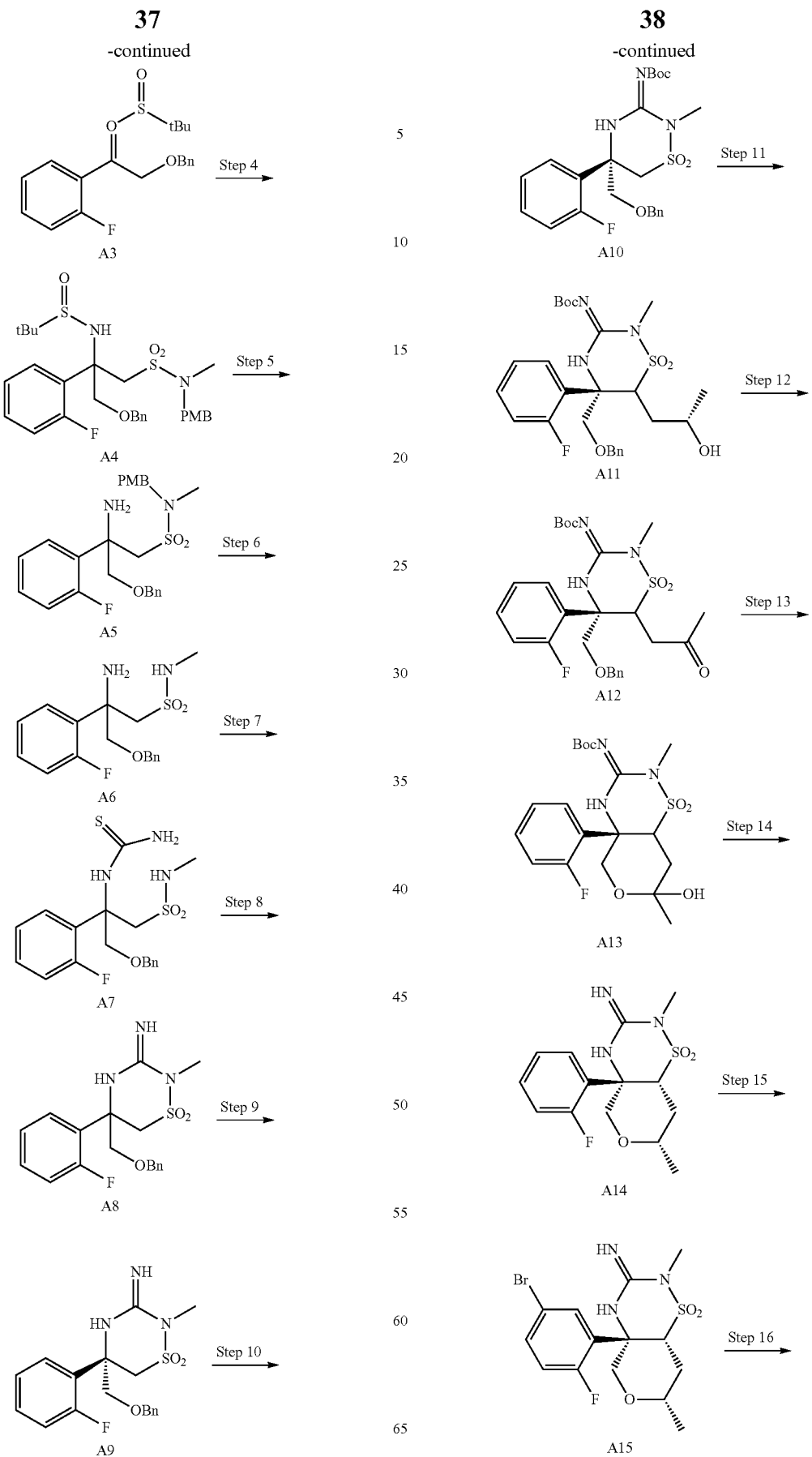

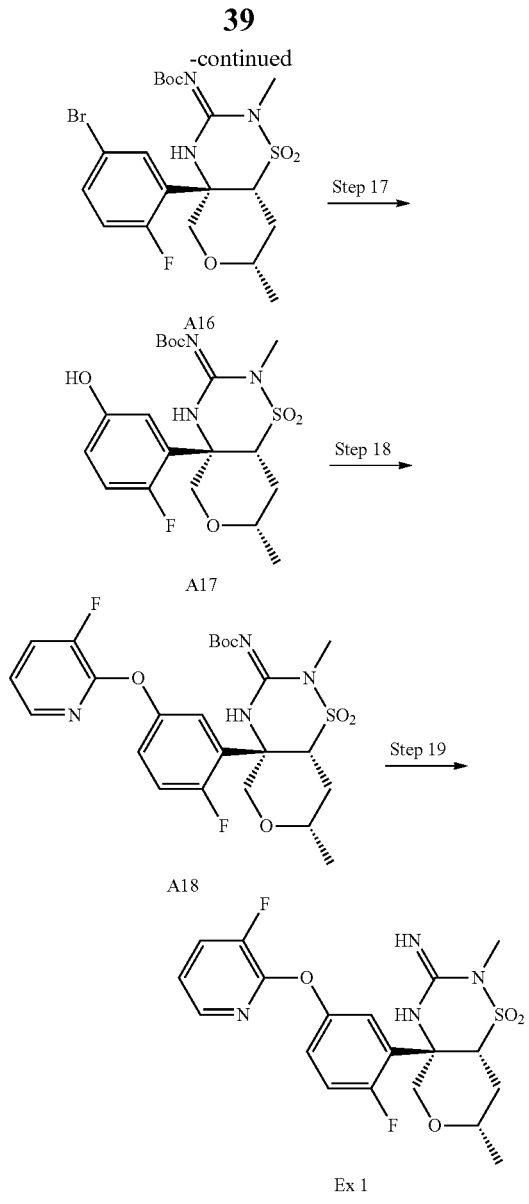

bined organic layers were dried over Na$_2$SO$_4$, filtered and concentrated. The residue was purified by silica gel chromatography (PE/EtOAc=120:1 to 40:1) to afford A2. MS for A2: m/e=245.1 (M+1).

Step 3

A solution of A2 (43 g, 180 mmol), tetraethoxytitanium (80 g, 350 mmol) and 2-methylpropane-2-sulfinamide (32 g, 260 mmol) in heptane (400 mL) was stirred at 70° C. for 0.5 h. The mixture was diluted with water (400 mL) and filtered through celite. The filter cake was washed with EtOAc (500 mL), and the resulting filtrate was washed with brine (100 mL), dried over Na$_2$SO$_4$, filtered and concentrated. The residue was purified by silica gel chromatography (PE/EtOAc=80:1 to 40:1 to 20:1) to afford A3. MS for A3: m/e=348.1 (M+1).

Step 4 n-Butyllithium (84 mL, 210 mmol, 2.5 M in hexane) was added dropwise to a solution of N-(4-methoxybenzyl)-N-methylmethanesulfonamide (41 g, 180 mmol) in THF (450 mL) at −78° C. The mixture was stirred at −78° C. for 1 h, then a solution of A3 (40 g, 120 mmol) in THF (50 mL) was added dropwise. The mixture was stirred at −78° C. for 4 h, then quenched with sat. NaHCO$_3$ aq (300 mL) and extracted with EtOAc (3×300 mL). The combined organic layers were washed with brine (100 mL), dried over Na$_2$SO$_4$, filtered and concentrated. The residue was purified by silica gel chromatography (PE/EtOAc=5:1 to 3:1) to afford A4. MS for A4: m/e=577.2 (M+1).

Step 5

HCl (40 mL, 160 mmol) (4 M in dioxane) was added to a solution of A4 (49 g, 54 mmol) in DCM (200 mL) at 0° C. and the mixture was stirred at 15° C. for 2 h. The mixture was concentrated to afford crude A5 as an orange oil which was used in the next step without further purification.

Step 6

To a solution of A5 (28 g, 59 mmol) in TFA (120 mL, 158 mmol) was added 2-mercaptoacetic acid (23 g, 250 mmol) at 0° C. The mixture was allowed to warm and stirred at 15° C. for 4 h, then concentrated and neutralized with sat. NaHCO$_3$ (aq. 1600 mL). The mixture was extracted with EtOAc (3×200 mL) and the combined organic extracts were washed with brine (100 mL), dried with Na$_2$SO$_4$, filtered and concentrated. The residue was purified by silica gel chromatography (PE/EtOAc=5:1 to 1.5:1) to afford A6. MS for A6: m/e=353.1 (M+1).

Step 7

A mixture of A6 (10 g, 64 mmol) and isothiocyanatobenzene (8.6 g, 77 mmol) in DCM (150 mL) was stirred at 15° C. for 16 h, then concentrated in vacuo. Separately, sodium (2.9 g, 130 mmol) was added to MeOH (30 mL) at 15° C. and the mixture was stirred at 15° C. for 15 min. The resulting solution was added to a solution of N-((1-(benzyloxy)-2-(2-fluorophenyl)-3-(N-methylsulfamoyl)propan-2-yl)carbamothioyl)benzamide (22 g, 43 mmol) in MeOH (200 mL) at 15° C. and the mixture was stirred at 15° C. for 3 hours. The mixture was concentrated, diluted with water (100 mL) and with EtOAc (3×40 mL). The combined organic layers were washed with brine (40 mL), dried over Na$_2$SO$_4$, filtered and concentrated to afford A7 as a brown solid which was used in the next step without further purification.

Step 8

Iodomethane (15 g, 110 mmol) was added to a solution of A7 (18 g, 43 mmol) in ethanol (200 mL) at 15° C. and the mixture was stirred at 15° C. for 16 hour. NaHCO$_3$ (7.2 g, 85 mmol) was added and the mixture was stirred at 60° C. for 3 hours, then cooled and concentrated in vacuo. Water Step 1

To a mixture of 1 (75 g, 450 mmol) and N1-((ethylimino)methyl)-N3,N3-dimethylpropane-1,3-diamine hydrochloride (130 g, 680 mmol) in DCM (700 mL) was added N,O-dimethylhydroxylamine hydrochloride (66.0 g, 680 mmol) and pyridine (75 mL, 450 mmol). The mixture was stirred at 25° C. for 16 h, then diluted with water (100 mL) and extracted with DCM (4×200 mL). The combined organic phases were washed with HCl (1 M, 200 mL) 3×, NaHCO$_3$ (sat., 200 mL) 2×, and brine (200 mL), then dried over Na$_2$SO$_4$, filtered and concentrated. The residue was purified by silica gel chromatography (PE/EtOAc=15:1 to 3:1) to provide A1.

Step 2 n-BuLi (120 mL, 290 mmol) (2.5 M in hexane) was added dropwise to a solution of 1-bromo-2-fluorobenzene (50 g, 290 mmol) in THF (500 mL) at −78° C. The mixture was stirred at -78° C. for 1 h., then a solution of A1 (50 g, 240 mmol) in THF (40 mL) was added dropwise and the mixture was stirred at −78° C. for 1 h. The reaction was quenched with NH$_4$Cl (sat., 150 mL) and water (200 mL). The mixture was then extracted with EtOAc (3×200 mL) and the com- (200 mL) was added and the mixture was extracted with EtOAc (3×60 mL). The organic layer was washed with brine (40 mL), dried over $Na_2SO_4$, filtered and concentrated. The residue was purified by silica gel chromatography (DCM/MeOH=50:1) to afford A8. MS for A8: m/e=378.1 (M+1).

Step 9

A8 (11 g, 26 mmol) was separated by SFC (Column: OJ(250 mm*50 mm, 10 um); Conditions: Base-ETOH; Begin B: 30%; End B: 30%; FlowRate (mL/min): 200 ML/MIN; Injections: 300) to afford A9 ($t_R$=2.088 min, rotation: −51.527, $CHCl_3$).

Step 10

A mixture of A9 (5.0 g, 13 mmol), triethylamine (2.7 g, 27 mmol) and di-tert-butyl dicarbonate (3.5 g, 16 mmol) in DCM (50 mL) was stirred at 15° C. for 16 h. The mixture was concentrated and purified by silica gel chromatography (PE/EtOAc=10:1) to afford A10. MS for A10: m/e=478.2 (M+1).

Step 11

A solution of A10 (7.0 g, 15 mmol) in THF (70 mL) was cooled to −20° C. under $N_2$ and lithium bis(trimethylsilyl) amide (44 mL, 44 mmol, 1 M in THF) was added. The reaction was stirred at this temp for 1 h, then a solution of (S)-2-methyloxirane (2.6 g, 44 mmol) in THF (2 mL) was added and the mixture was stirred at 15° C. for 3 h. The reaction was quenched with $NH_4Cl$ (sat, 70 mL) and extracted with EtOAc (3×50 mL). The combined organic layers were dried over $Na_2SO_4$, filtered and concentrated. The residue was purified by silica gel chromatography (PE/EtOAc=4:1) to give A11. MS for A11: m/e=536.2 (M+1).

Step 12

To a solution of A11 (6.0 g, 11 mmol) in DCM (50 mL) was added DMP (9.5 g, 22 mmol) at 0° C. and the mixture was stirred at 15° C. for 3 h. The mixture was diluted with sat. $NaHCO_3$ (80 mL) and sat. $Na_2SO_3$ (80 mL). After 30 min, the mixture was extracted with DCM (3×45 mL) and the combined organic layers was dried over $Na_2SO_4$, filtered and concentrated. The residue was purified by silica gel chromatography (PE/EtOAc=5:1) to afford A12. MS for A12: m/e=534.2 (M+1).

Step 13

To a solution of A12 (5.0 g, 9.4 mmol) in MeOH (50 mL) was added $Pd(OH)_2$ (20%, 5.0 g, 7.1 mmol) and hydrogen chloride (0.3 mL, 1.2 mmol) (4 M in dioxane). The mixture was stirred at 15° C. under $H_2$ 15 psi for 4 h, then filtered through celite and concentrated. The residue was purified by silica gel chromatography (PE/EtOAc=7:1) to afford A13. MS for A13: m/e=444.2 (M+1).

Step 14

To a solution of A13 (2.3 g, 5.2 mmol) in TFA (10 mL, 130 mmol) and 1,2-dichloroethane (10 mL) was added triethylsilane (9.1 g, 78 mmol) at 0° C., followed by addition of 4A MS (200 mg). The mixture was stirred at 45° C. for 4 h, then filtered and the filtrate was concentrated in vacuo. The resulting residue was diluted with sat. $NaHCO_3$ aq. (60 mL) and extracted with DCM (3×30 mL). The combined organic layers were washed with brine (20 mL), dried over $Na_2SO_4$ and concentrated. The residue was purified by silica gel chromatography (DCM/MeOH=20:1) to afford A14. MS for A14: m/e=328.1 (M+1).

Step 15

To a solution of A14 (600 mg, 1.8 mmol) in acetonitrile (6 mL) was added 1,3-dibromo-5,5-dimethylimidazolidine-2,4-dione (790 mg, 2.8 mmol). The mixture was cooled to 0° C. and added dropwise slowly sulfuric acid (0.59 mL, 11 mmol) with efficient stirring to maintain the internal temperature below 15° C. On completion of addition, the cooling bath was removed and the mixture was stirred a further 10 min at 15° C. The vessel was then transferred to a preheated oil bath at 55° C. and the mixture heated for 5 h. The mixture was poured into water (60 mL), adjusted to pH=7 with sat. $NaHCO_3$ and extracted with EtOAc (3×40 mL). The organic layer was combined, dried over $Na_2SO_4$, filtered and concentrated to give A15 which was used in the next step without further purification.

Step 16

To a solution of A15 (820 mg, 2.0 mmol) in $CH_2Cl_2$ (8 mL) was added di-tert-butyl dicarbonate (880 mg, 4.0 mmol) and triethylamine (610 mg, 6.1 mmol). The mixture was stirred at 20° C. for 16 h, then concentrated and purified by silica gel chromatography (PE/EtOAc=6:1) to afford A16. MS for A16: m/e=506.1 and 508.1 (M+1).

Step 17

To a solution of A16 (410 mg, 0.810 mmol) in MeOH (4 mL) was added DIEA (0.42 mL, 2.4 mmol), hypodiboric acid (150 mg, 1.6 mmol) and chloro[(tricyclohexylphosphine)-2-(2'-aminobiphenyl)]palladium(II) (48 mg, 0.081 mmol). The mixture was stirred at 15° C. for 2 h, then concentrated in vacuo. The resulting residue was re-dissolved in $CH_2Cl_2$ (10 mL), treated with hydrogen peroxide (920 mg, 8.1 mmol) (30% in $H_2O$) and stirred at 15° C. for 0.5 h. The mixture was concentrated in vacuo and the resulting residue was purified by silica gel chromatography (PE/EtOAc=7:1) to afford A17. MS for A17: m/e=444.2 (M+1).

Step 18

A mixture of A17 (60 mg, 0.10 mmol), 2,3-difluoropyridine (24 mg, 0.21 mmol) and $Cs_2CO_3$ (101 mg, 0.308 mmol) in DMSO (1 mL) was stirred at 65° C. for 2 h. The mixture was diluted with water (30 mL) and extracted with EtOAc (3×25 mL). The combined organic layers were dried over $Na_2SO_4$ and filtered to afford the crude product of A18, which was used in the next step directly without further purification.

Step 19

TFA (0.5 mL, 6.5 mmol) was added to a solution of A18 (60 mg, 0.056 mmol) in DCM (2.5 mL). The mixture was stirred at 15° C. for 2 h, then concentrated and purified by p-HPLC (TFA) to afford Example 1.

| Ex | Structure<br>HNMR<br>IUPAC Name | LCMS m/z (M + 1) | BACE-1 $K_i$ (nM) | BACE-2 $K_i$ (nM) |
|---|---|---|---|---|
| 1 | 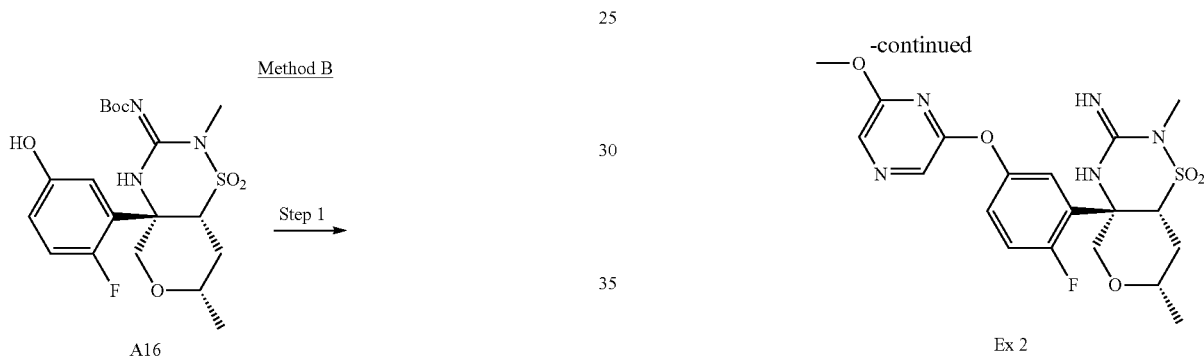<br>δ (400 MHz, CDCl₃): 1.37 (3 H, d, J = 6.0 Hz), 1.67-1.60 (1 H, m), 2.36-2.26 (1 H, m,), 3.29 (3 H, s), 3.77 (1 H, dd, J = 5.8, 10.3 Hz), 3.93 (1 H, d, J = 12.8 Hz), 4.21 (1 H, d, J = 12.8 Hz), 4.73-4.63 (1 H, m), 7.03-6.95 (1 H, m), 7.24-7.12 (3 H, m), 7.46 (1 H, t, J = 8.5 Hz), 7.88 (1 H, d, J = 4.0 Hz).<br>(4aS,7S,8aR)-4a-(2-fluoro-5-((3-fluoropyridin-2-yl)oxy)phenyl)-3-imino-2,7-dimethyloctahydropyrano[3,4-e][1,2,4]thiadiazine 1,1-dioxide | 439.1 | 3.4 | 1.6 |

Method B

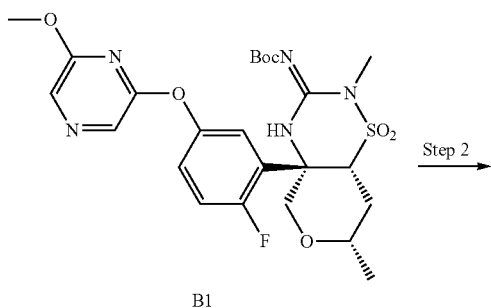

Step 1

To a solution of A16 (25 mg, 0.056 mmol) and 2-fluoro-6-methoxypyrazine (14 mg, 0.11 mmol) in DMSO (0.5 mL) was added Cs₂CO₃ (37 mg, 0.11 mmol) and the mixture was stirred at 60° C. for 1 h. The mixture was quenched with water (15 mL) and extracted with EtOAc (4×25 mL). The combined organic extracts were washed with brine (10 mL), dried over Na₂SO₄, filtered and concentrated to provide B1 as brown oil which was used in the next step without further purification. MS for B1 m/e=552.2 (M+1).

Step 2

TFA (0.5 mL, 6.5 mmol) was added to a solution of B1 (30 mg, 0.054 mmol) in DCM (2.5 mL). The mixture was stirred at 15° C. for 2 h, then concentrated and purified by p-HPLC (TFA) to afford Example 2.

Example 3 was prepared in an analogous fashion using Method B and replacing 2-fluoro-6-methoxypyrazine with the appropriate reagent in step 1.

| Ex | Structure | LCMS m/z (M + 1) | BACE-1 K$_i$ (nM) | BACE-2 K$_i$ (nM) |
|---|---|---|---|---|
| | HNMR | | | |
| | IUPAC Name | | | |
| 2 | 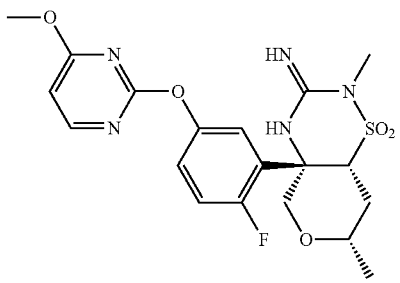 | 452.1 | 7.3 | 9.6 |

δ (400 MHz, CDCl$_3$): 1.38 (3 H, d, J = 5.9 Hz), 1.66-1.57 (1 H, m), 2.32 (1 H, d, J = 10.2 Hz), 3.29 (3 H, s), 3.72 (3 H, s), 3.78 (1 H, dd, J = 6.5, 10.8 Hz), 3.94 (1 H, d, J = 12.9 Hz), 4.16 (1 H, d, J = 12.9 Hz), 4.75-4.57 (1 H, m) 7.22-7.05 (3 H, m), 7.88 (2 H, d, J = 14.5 Hz).

(4aS,7S,8aR)-4a-(2-fluoro-5-(((6-methoxypyrazin-2-yl)oxy)phenyl)-3-imino-2,7-dimethyloctahydropyrano[3,4-e][1,2,4]thiadiazine 1,1-dioxide

| 3 | | 446.1 | 2.7 | 2.3 |

δ (400 MHz, CDCl$_3$): 1.38 (3 H, d, J = 5.9 Hz), 1.62-1.54 (1 H, m), 2.33 (1 H, dd, J = 3.1, 13.7 Hz), 3.30 (3 H, s), 3.85-3.71 (1 H, m), 3.95 (1 H, d, J = 12.5 Hz), 4.20 (1 H, d, J = 12.9 Hz), 4.73-4.59 (1 H, m) 7.24-7.09 (5 H, m), 8.28 (1 H, d, J = 4.7 Hz).

2-(4-fluoro-3-((4aS,7S,8aR)-3-imino-2,7-dimethyl-1,1-dioxidooctahydropyrano[3,4-e][1,2,4]thiadiazin-4a-yl)phenoxy)isonicotinonitrile

Method C

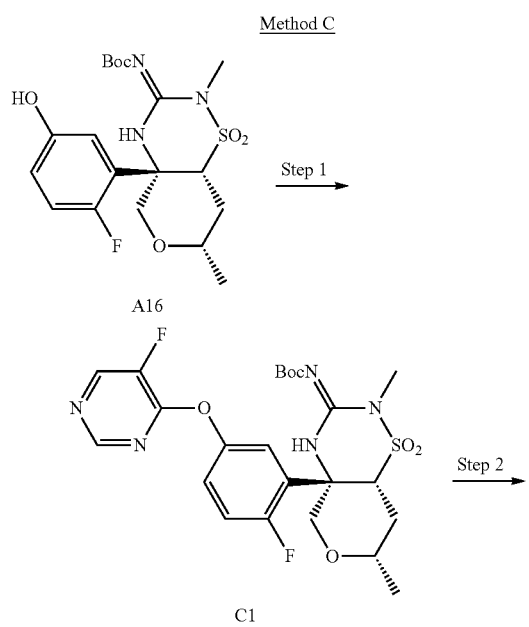

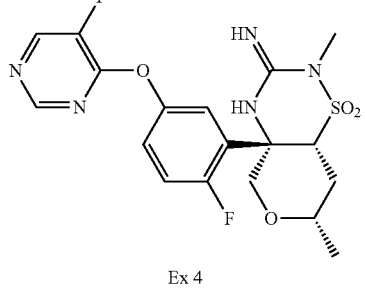

Step 1
To a solution of A16 (25 mg, 0.056 mmol) and 4-chloro-5-fluoropyrimidine (15 mg, 0.11 mmol) in DMSO (0.5 mL) was added $Cs_2CO_3$ (37 mg, 0.11 mmol) and the mixture was stirred at 15° C. for 35 mins. The mixture was quenched with water (15 mL) and extracted with EtOAc (4×25 mL). The combined organic extracts were washed with brine (10 mL), dried over $Na_2SO_4$, filtered and concentrated to provide C1 as brown oil which was used in the next step without further purification. MS for C1 m/e=540.2 (M+1).

Step 2
TFA (0.5 mL, 6.5 mmol) was added to a solution of C1 (30 mg, 0.056 mmol) in DCM (2.5 mL). The mixture was stirred at 15° C. for 2 h, then concentrated and purified by p-HPLC (TFA) to afford Example 4.

| Ex | Structure / IUPAC Name / HNMR | LCMS m/z (M + 1) | BACE-1 $K_i$ (nM) | BACE-2 $K_i$ (nM) |
|---|---|---|---|---|
| 4 | (4aS,7S,8aR)-4a-(2-fluoro-5-((5-fluoropyrimidin-4-yl)oxy)phenyl)-3-imino-2,7-dimethyloctahydropyrano[3,4-e][1,2,4]thiadiazine 1,1-dioxide<br><br>δ (400 MHz, $CDCl_3$): 1.38 (3 H, d, J = 5.9 Hz), 1.69-1.59 (1 H, m), 2.37-2.29 (1 H, m), 3.30 (3 H, s), 3.85-3.72 (1 H, m), 3.95 (1 H, d, J = 12.9 Hz), 4.21 (1 H, d, J = 12.9 Hz), 4.73-4.63 (1 H, m), 7.24-7.15 (1 H, m), 7.31 (2 H, d, J = 6.3 Hz), 8.48 (2 H, s). | 440.1 | 12 | 5.9 |

Method D

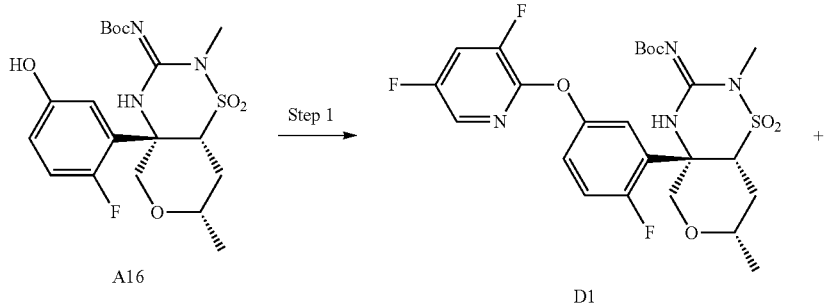

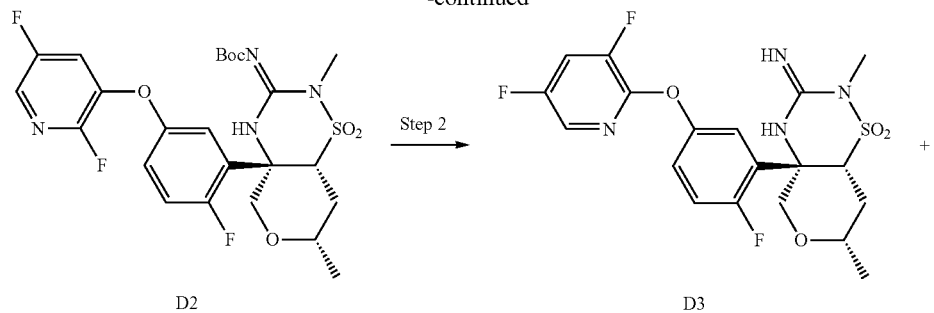

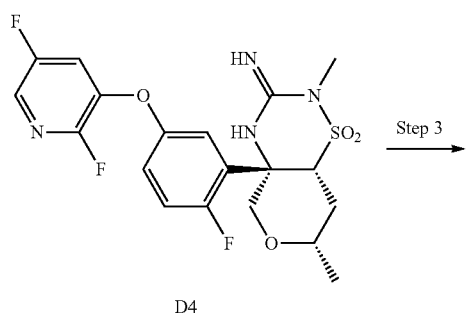

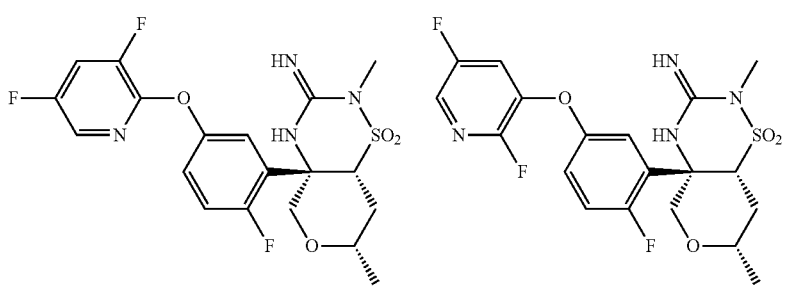

Step 1

To a solution of A16 (50 mg, 0.11 mmol) and 2,3,5-trifluoropyridine (30.0 mg, 0.23 mmol) in DMSO (2 mL) was added $Cs_2CO_3$ (74 mg, 0.225 mmol) and the mixture was stirred at 60° C. for 1 h. The reaction mixture was quenched with water (15 mL) and extracted with EtOAc (4×25 mL). The combined organic extracts were washed with brine (10 mL), dried over $Na_2SO_4$, filtered and concentrated to give a mixture of D1/D2 as brown oil which was used in the next step without further purification.

Step 2

TFA (0.5 mL, 6.5 mmol) was added to a solution of a mixture of D1/D2 (60 mg, 0.11 mmol) in DCM (2.5 mL). The mixture was stirred at 15° C. for 2 h, then concentrated and purified by p-HPLC (TFA) to afford a mixture of D3/D4.

Step 3

The mixture of D3/D4 (30 mg, 0.066 mmol) was separated by SFC (Column AD, 250 mm×30 mm, 5 um) to give Example 5 ($t_R$=2.564 min) and Example 6 ($t_R$=2.779 min).

| Ex | Structure HNMR IUPAC Name | LCMS m/z (M + 1) | BACE-1 K$_i$ (nM) | BACE-2 K$_i$ (nM) |
|---|---|---|---|---|
| 5 | ![structure] δ (400 MHz, MeOH-d): 1.31 (3 H, d, J = 6.3 Hz), 1.75 (1 H, q, J = 11.9 Hz), 2.32 (1 H, dd, J = 2.5, 13.5 Hz), 3.24 (3 H, s), 3.84 (1 H, dd, J = 6.1, 9.6 Hz), 3.98 (2 H, q, J = 12.7 Hz), 5.08 (1 H, td, J = 4.2, 8.0 Hz), 7.31-7.13 (3 H, m), 7.77-7.67 (1 H, m), 7.85 (1 H, d, J = 2.3 Hz). (4aS,7S,8aR)-4a-(5-((3,5-difluoropyridin-2-yl)oxy)-2-fluorophenyl)-3-imino-2,7-dimethyloctahydropyrano[3,4-e][1,2,4]thiadiazine 1,1-dioxide | 457.1 | 25 | 13 |
| 6 | ![structure] δ (400 MHz, MeOH-d): 1.31 (3 H, d, J = 6.3 Hz), 1.81-1.64 (1 H, m), 2.30 (1 H, dd, J = 2.5, 13.5 Hz), 3.24 (3 H, s), 3.83 (1 H, dd, J = 5.7, 9.6 Hz), 4.09-3.93 (2 H, m), 5.09-5.00 (1 H, m), 7.11 (1 H, br. s.), 7.23-7.15 (1 H, m), 7.36-7.25 (2 H, m), 7.90-7.80 (1 H, m). (4aS,7S,8aR)-4a-(5-((2,5-difluoropyridin-3-yl)oxy)-2-fluorophenyl)-3-imino-2,7-dimethyloctahydropyrano[3,4-e][1,2,4]thiadiazine 1,1-dioxide | 457.1 | 7.1 | 15 |

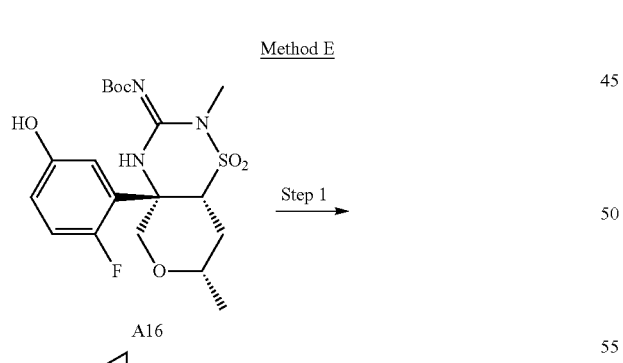

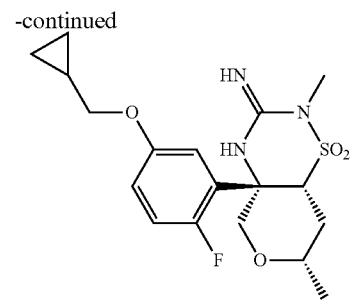

Ex 7

Step 1

To a solution of A16 (25 mg, 0.056 mmol) and (bromomethyl)cyclopropane (15 mg, 0.11 mmol) in DMSO (0.5 mL) was added Cs$_2$CO$_3$ (37 mg, 0.11 mmol) and the mixture was stirred at 60° C. for 2 h. The reaction mixture was quenched with water (15 mL) and extracted with EtOAc (4×25 mL). The combined extracts were washed with brine (10 mL), dried over Na$_2$SO$_4$, filtered and concentrated to provide E1 as brown oil which was used in the next step without further purification. MS for E1 m/e=498.2 (M+1).

Step 2

TFA (0.5 mL, 6.5 mmol) was added to a solution of E1 (50 mg, 0.012 mmol) in DCM (2.5 mL). The mixture was stirred at 15° C. for 2 h, then concentrated and purified by p-HPLC (TFA) to afford Example 7.

Example 8 was prepared in an analogous fashion using Method E replacing (bromomethyl)cyclopropane with reagent L1 in step 1.

| Ex | Structure HNMR IUPAC Name | LCMS m/z (M + 1) | BACE-1 $K_i$ (nM) | BACE-2 $K_i$ (nM) |
|---|---|---|---|---|
| 7 | 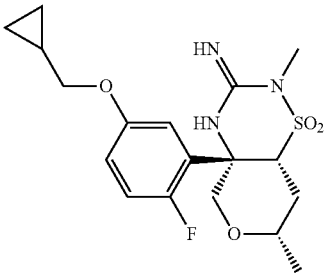 δ (400 MHz, CDCl$_3$): 0.36-0.32 (2 H, m), 0.66-0.63 (2 H, m), 1.19-1.16 (1 H, m), 1.38 (3 H, d, J = 6.2 Hz), 2.03-2.01 (1 H, m), 2.37-2.33 (1 H, m), 3.28 (3 H, s), 3.88-3.71 (4 H, m), 4.30-4.11 (2 H, m), 6.90-6.85 (1 H, m), 7.23-7.18 (1 H, m), 7.63-7.49 (1 H, m). (4aS,7S,8aR)-4a-(5-(cyclopropylmethoxy)-2-fluorophenyl)-3-imino-2,7-dimethyloctahydropyrano[3,4-e][1,2,4]thiadiazine 1,1-dioxide | 398.1 | 28 | 4.3 |
| 8 | 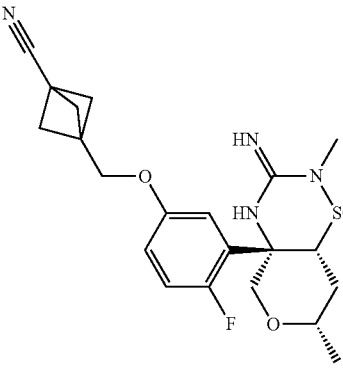 δ (400 MHz, CDCl$_3$): 1.38 (3 H, d, J = 6.2 Hz), 2.04-1.99 (1 H, m), 2.37-2.23 (7 H, m), 3.34 (3 H, s), 3.86-3.67 (2 H, m), 3.95-3.87 (2 H, m), 4.09 (1 H, d, J = 12.8 Hz), 4.83-4.69 (1 H, m), 6.89-6.75 (2 H, m), 7.01 (1 H, dd, J = 8.9, 11.8 Hz). 3-((4-fluoro-3-((4aS,7S,8aR)-3-imino-2,7-dimethyl-1,1-dioxidooctahydropyrano[3,4-e][1,2,4]thiadiazin-4a-yl)phenoxy)methyl)bicyclo[1.1.1]pentane-1-carbonitrile | 449.1 | 9.1 | 28 |

Method F

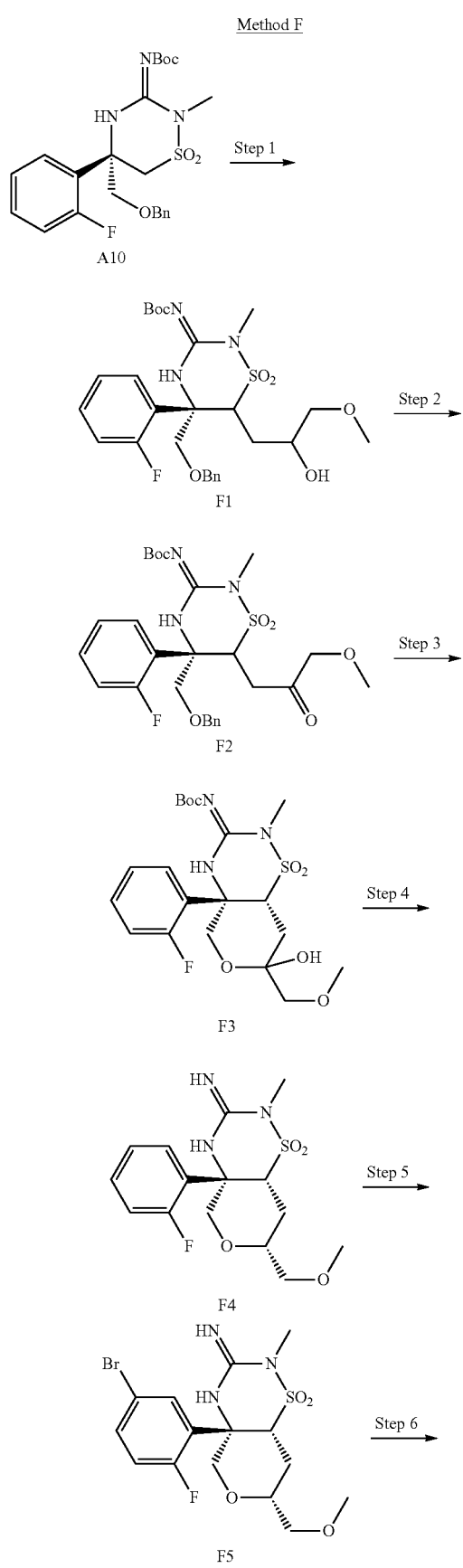

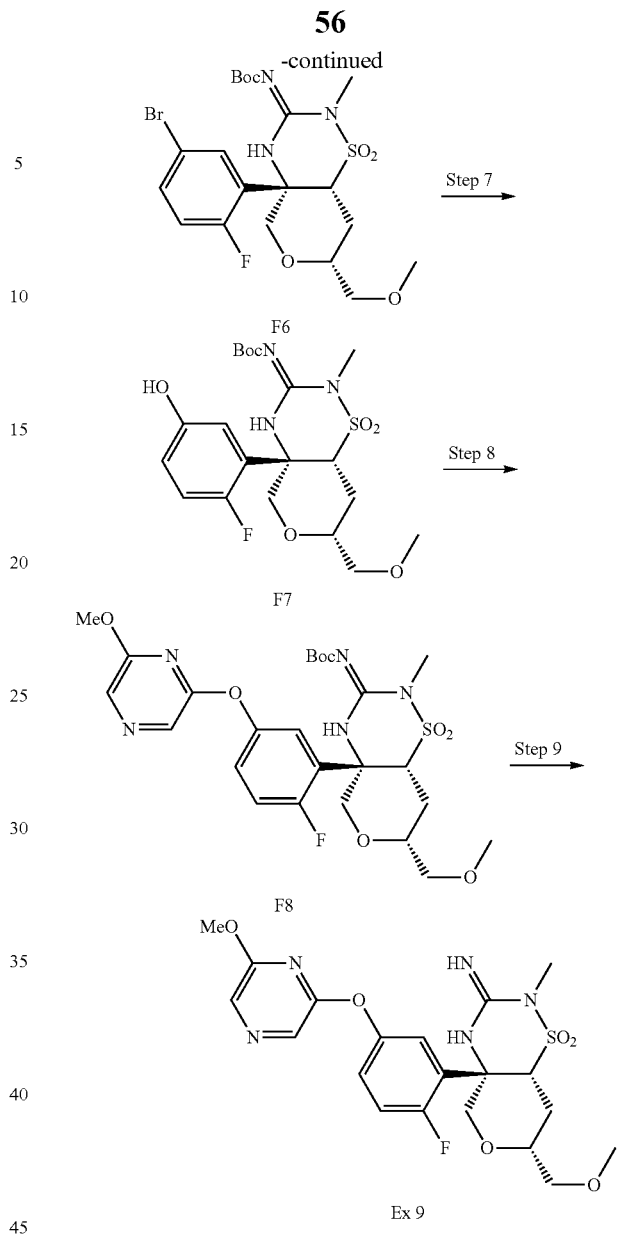

Step 1

To a solution of A10 (6.0 g, 13 mmol) in THF (70 mL) was added LiHMDS (38 mL, 38 mmol, 1 M in THF) at −20° C. After stirring for 1 h, 2-(methoxymethyl)oxirane (2.2 g, 25 mmol) was added at −20° C. and the mixture warmed slowly to 20° C. and stirred for 4 h. The reaction mixture was quenched with sat. NH$_4$Cl (70 mL), extracted with EtOAc (3×50 mL) and the combined organic layers were washed with brine (30 mL), dried over Na$_2$SO$_4$, filtered and concentrated in vacuo. The resulting residue was purified by silica gel chromatography (PE/EtOAc=5:1) to afford F1. MS for F1 m/e=566.2 (M+1).

Step 2

A mixture of F1 (6.7 g, 12 mmol) and DMP (10 g, 24 mmol) in DCM (70 mL) was stirred at 20° C. for 16 h. The reaction mixture was quenched with sat. (Na$_2$SO$_3$) (100 mL) and sat. NaHCO$_3$ (100 mL) and after stirring 30 min was extracted with DCM (3×80 mL). The combined organic layers were washed with brine (40 mL), dried over Na$_2$SO$_4$, filtered and concentrated in vacuo. The resulting residue was purified by silica gel chromatography (PE/EtOAc=5:1) to afford F2. MS for F2 m/e=564.1 (M+1).

Step 3

A mixture of F2 (4.3 g, 7.6 mmol), HCl/Dioxane (0.2 mL, 0.80 mmol) (4 M) and Pd(OH)$_2$ (20%, 4.0 g, 5.7 mmol) in MeOH (60 mL) was stirred at 20° C. for 2 h under a H$_2$ (15 psi) atmosphere. The mixture was filtered through Celite and the filtrate was concentrated in vacuo. The resulting residue was purified by silica gel chromatography (PE/EtOAc=4.5:1) to afford F3. MS for F3 m/e=474.2 (M+1).

Step 4

To a solution of F3 (1.3 g, 2.7 mmol), BF$_3$.OEt$_2$ (24 mL, 190 mmol) and DCM (12 mL) was added triethylsilane (24 g, 210 mmol) and MS (4A) (5 g) at 0° C. The reaction mixture was stirred at 20° C. for 60 h, then neutralized with sat. Na$_2$CO$_3$ (500 mL) and extracted with DCM (3×50 mL). The combined organic layers were washed with brine (50 mL), dried over Na$_2$SO$_4$, filtered and concentrated in vacuo to afford F4, which was used in the next step without further purification. MS for F4 m/e=358.1 (M+1).

Step 5

To a solution of F4 (1.0 g, 2.8 mmol) in acetonitrile (10 mL) was added 1,3-dibromo-5,5-dimethylimidazolidine-2,4-dione (1.2 g, 4.2 mmol). The mixture was cooled to 0° C. and treated dropwise slowly with sulfuric acid (0.60 mL, 11 mmol) with efficient stirring to maintain the internal temperature below 20° C. On completion of addition, the cooling bath was removed and the mixture stirred a further 10 min at 20° C. The vessel was then transferred to a preheated oil bath at 55° C. and the mixture heated at 55° C. for 4 h. The mixture was poured into water (60 mL), adjusted to pH=7 with sat. NaHCO$_3$ and extracted with EtOAc (3×40 mL). The organic layer was combined, dried over Na$_2$SO$_4$, filtered and concentrated to provide F5, which was used in the next step without further purification. MS for F5 m/e=436.1 and 438.1 (M+1).

Step 6

To a solution of F5 (1.6 g, 2.6 mmol) in DCM (6 mL) was added Boc$_2$O (1.8 mL, 7.7 mmol), followed by triethylamine (1.8 mL, 13 mmol). The mixture was stirred at 20° C. for 18 h, then concentrated in vacuo and purified by silica gel chromatography (PE/EtOAc=6:1) to provide F6. MS for F6 m/e=536.1 and 538.1 (M+1).

Step 7

To a solution of F6 (900 mg, 1.7 mmol) in MeOH (10 mL) was added DIEA (0.88 mL, 5.0 mmol), hypodiboric acid (300 mg, 3.4 mmol) and chloro[(tricyclohexylphosphine)-2-(2'-aminobiphenyl)]palladium(II) (99 mg, 0.17 mmol). The mixture was stirred at 25° C. under N$_2$ for 0.5 h, then concentrated. The resulting residue was re-dissolved in CH$_2$Cl$_2$ (10 mL), followed by addition of hydrogen peroxide (950 mg, 8.4 mmol) (30% in H$_2$O) and stirred at 25° C. for 2 h. The reaction was slowly quenched with sat. Na$_2$SO$_3$ aq. (60 mL). The mixture was extracted with DCM (3×30 mL) and the combined organic layers were washed with brine (20 mL), dried over Na$_2$SO$_4$, filtered and concentrated. The residue was purified by silica gel chromatography (PE/EtOAc=6:1) to afford F7. MS for F7 m/e=474.2 (M+1).

Step 8

To a solution of F7 (25 mg, 0.053 mmol) and 2-chloro-6-methoxypyrazine (15 mg, 0.11 mmol) in DMSO (0.5 mL) was added Cs$_2$CO$_3$ (37 mg, 0.11 mmol) and the mixture was stirred at 60° C. for 1 h. The reaction mixture was quenched with water (15 mL) and extracted with EtOAc (3×25 mL). The combined organic extracts were washed with brine (10 mL), dried over Na$_2$SO$_4$, filtered and concentrated to provide F8, which was used in the next step without further purification. MS for F8 m/e=582.2 (M+1).

Step 9

TFA (0.5 mL, 6.5 mmol) was added to a solution of F8 (35 mg, 0.060 mmol) in DCM (2.5 mL). The mixture was stirred at 25° C. for 1 h, then concentrated and purified by p-HPLC (TFA) to afford Example 9.

Example 10 was prepared in an analogous fashion using Method F. replacing 2-chloro-6-methoxypyrazine with the appropriate reagent in step 8.

| Ex | Structure / HNMR / IUPAC Name | LCMS m/z (M + 1) | BACE-1 K$_i$ (nM) | BACE-2 K$_i$ (nM) |
| --- | --- | --- | --- | --- |
| 9 | (structure shown) | 482.1 | 4.6 | 9.4 |

δ (400 MHz, CDCl$_3$): 1.79 (1 H, s), 2.37 (1 H, dd, J = 3.1, 13.3 Hz), 3.29 (3 H, s), 3.42 (3 H, s), 3.53-3.46 (1 H, m), 3.66-3.54 (1 H, m), 3.71 (3 H, s), 3.89-3.79 (m,1 H), 3.95 (1 H, d, J = 12.5 Hz), 4.21 (1 H, d, J = 12.9 Hz), 4.74-4.63 (1 H, m), 7.20-7.10 (3 H, m), 7.88 (2 H, d, J = 13.7 Hz).

(4aS,7R,8aR)-4a-(2-fluoro-5-((6-methoxypyrazin-2-yl)oxy)phenyl)-3-imino-7-(methoxymethyl)-2-methyloctahydropyrano[3,4-e][1,2,4]thiadiazine 1,1-dioxide

| 10 | 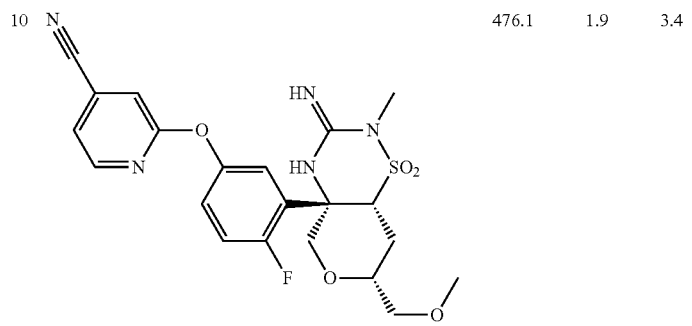 | 476.1 | 1.9 | 3.4 |

δ (400 MHz, CHCl₃): 1.84-1.75 (1 H, m), 2.38 (1 H, dd, J = 3.3, 13.1 Hz), 3.30 (3 H, s), 3.42 (3 H, s), 3.50 (1 H, dd, J = 4.5, 10.0 Hz), 3.65-3.56 (1 H, m), 3.89-3.76 (1 H, m), 3.97 (1 H, d, J = 12.9 Hz), 4.25 (1 H, d, J = 12.9 Hz), 4.74-4.60 (1 H, m), 7.19 (5 H, dt, J = 4.7, 10.6 Hz), 8.28 (1 H, d, J = 5.1 Hz).

2-(4-fluoro-3-((4aS,7R,8aR)-3-imino-7-(methoxymethyl)-2-methyl-1,1-dioxidooctahydropyrano[3,4-e][1,2,4]thiadiazin-4a-yl)phenoxy)isonicotinonitrile

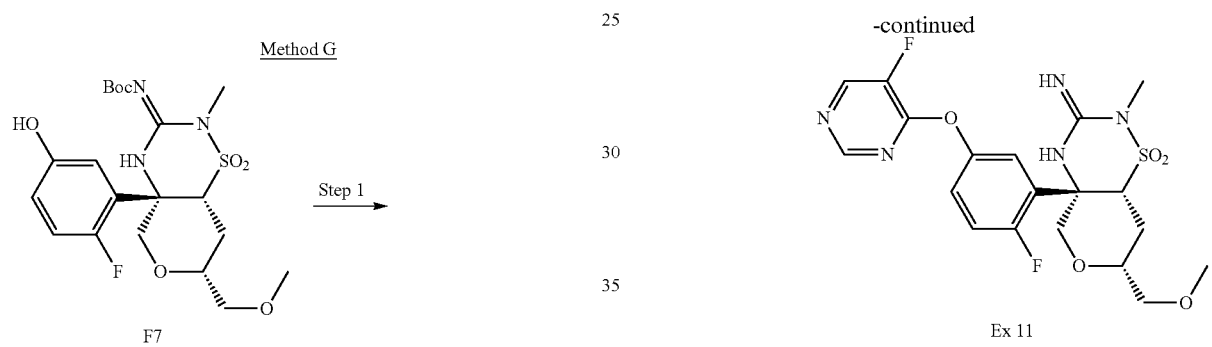

Method G

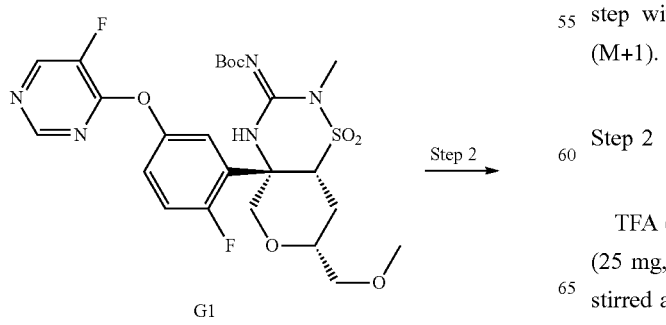

Step 1

To a solution of F7 (25 mg, 0.053 mmol) and 4-chloro-5-fluoropyrimidine (8.4 mg, 0.063 mmol) in DMSO (0.5 mL) was added Cs₂CO₃ (37 mg, 0.11 mmol) and the mixture was stirred at 25° C. for 20 mins. The resulting mixture was quenched with water (15 mL) and extracted with EtOAc (3×15 mL). The combined organic extracts were washed with brine (10 mL), dried over Na₂SO₄, filtered and concentrated to provide crude G1, which was used in the next step without further purification. MS for G1 m/e=570.2 (M+1).

Step 2

TFA (500 mg, 4.4 mmol) was added to a solution of G1 (25 mg, 0.039 mmol) in DCM (2.5 mL). The mixture was stirred at 25° C. for 1 h, then concentrated and purified by p-HPLC (TFA) to afford Example 11.

| Ex | Structure HNMR IUPAC Name | LCMS m/z (M + 1) | BACE-1 $K_i$ (nM) | BACE-2 $K_i$ (nM) |
|---|---|---|---|---|
| 11 | | 470.1 | 5.9 | 4.5 |
δ (400 MHz, CDCl$_3$): 1.83-1.77 (1 H, m), 2.39 (1 H, dd, J = 3.1, 13.7 Hz), 3.29 (3 H, s), 3.42 (3 H, s), 3.50 (1 H, dd, J = 4.5, 10.4 Hz), 3.62 (1H, dd, J = 5.5, 10.2 Hz), 3.91-3.78 (1 H, m), 3.97 (1 H, d, J = 12.5 Hz), 4.28 (1 H, d, J = 12.9 Hz), 4.74-4.63 (1 H, m), 7.31-7.17 (3 H, m), 8.47 (2 H, s).
(4aS,7R,8aR)-4a-(2-fluoro-5-((5-fluoropyrimidin-4-yl)oxy)phenyl)-3-imino-7-(methoxymethyl)-2-methyloctahydropyrano[3,4-e][1,2,4]thiadiazine 1,1-dioxide
Method H
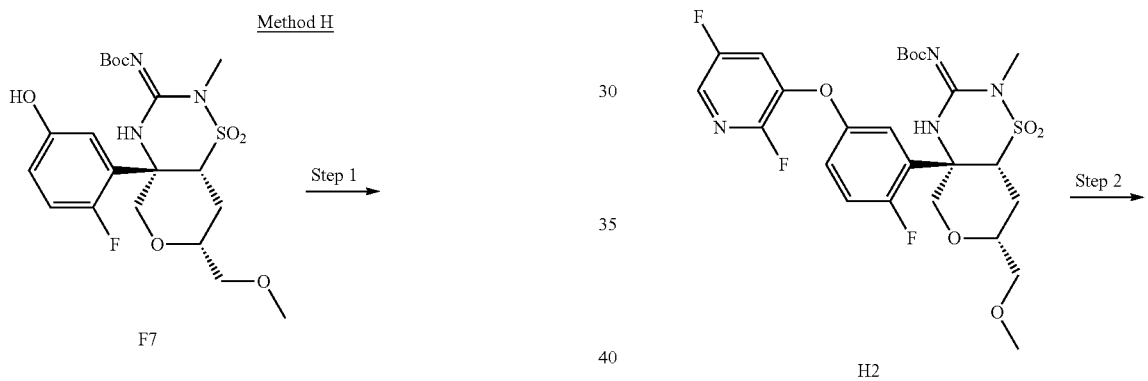
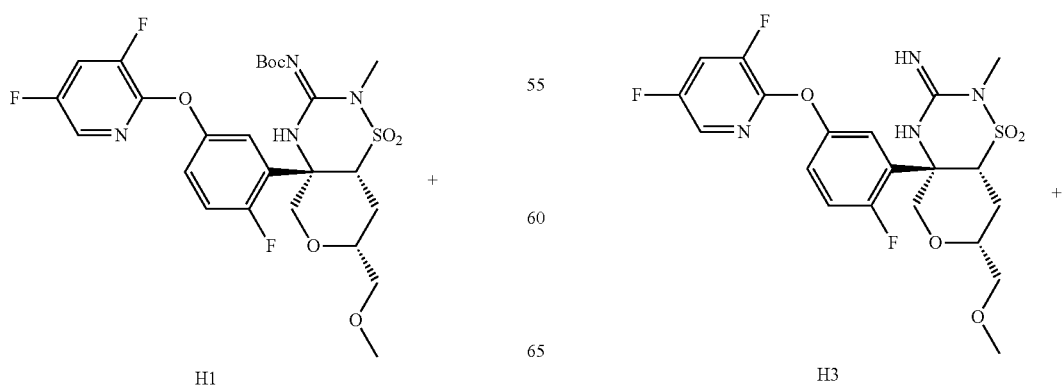

-continued

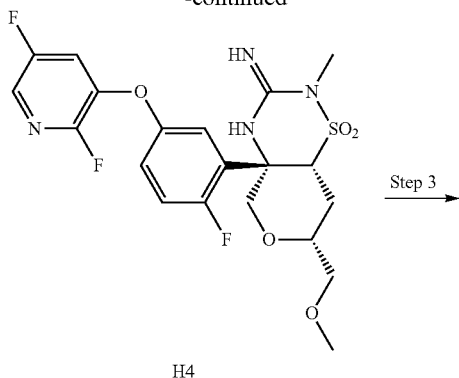

H4

Step 3 →

-continued

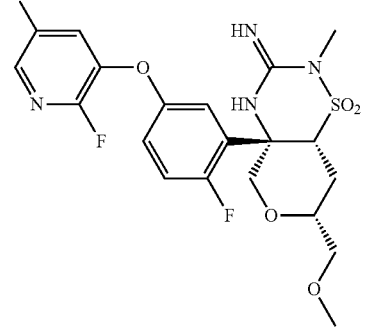

Ex 13

Step 1

To a solution of F7 (50 mg, 0.11 mmol) and 2,3,5-trifluoropyridine (28 mg, 0.21 mmol) in DMSO (1 mL) was added $Cs_2CO_3$ (69 mg, 0.21 mmol) and the mixture was stirred at 60° C. for 1 h. The reaction mixture was quenched with water (15 mL) and extracted with EtOAc (4×25 mL). The combined organic extracts were washed with brine (10 mL), dried over $Na_2SO_4$, filtered and concentrated to provide a crude mixture of H1/H2, which was used in the next step without further purification.

Step 2

TFA (500 mg, 4.4 mmol) was added to a solution of a mixture of H1/H2 (50 mg, 0.085 mmol) in DCM (2.5 mL). The mixture was stirred at 25° C. for 1 h, then concentrated and purified by p-HPLC (TFA) to afford a mixture of H3/H4.

Step 3

A mixture of H3/H4 (40 mg, 0.082 mmol) was separated by SFC (Column AD, 250 mm×30 mm, 5 um) to afford Example 12 ($t_R$=2.82 min) and Example 13 ($t_R$=3.01 min).

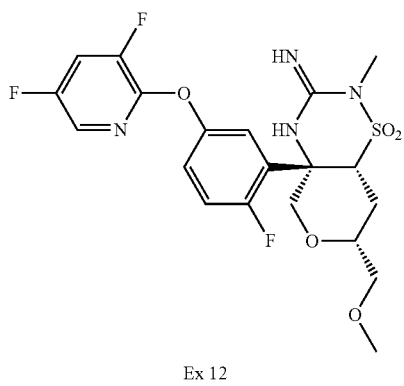

Ex 12

| Ex | Structure / IUPAC Name / HNMR | LCMS m/z (M + 1) | BACE-1 $K_i$ (nM) | BACE-2 $K_i$ (nM) |
|---|---|---|---|---|
| 12 | (structure shown below) | 487.1 | 20 | 18 |

δ (400 MHz, $CDCl_3$): 1.83-1.68 (1 H, m), 2.22 (1 H, dd, J = 2.9, 13.1 Hz,), 3.20 (3 H, s), 3.40 (3 H, s), 3.50-3.47 (1 H, m), 3.56-3.53 (1 H, m), 3.82-3.77 (1 H, m), 3.95-3.88 (1 H, m), 4.06-3.98 (1 H, m), 4.54 (1 H, td, J = 4.6, 12.3 Hz), 7.15-7.01 (2 H, m), 7.37-7.27 (2 H, m), 7.80 (1 H, d, J = 2.0 Hz).

(4aS,7R,8aR)-4a-(5-((3,5-difluoropyridin-2-yl)oxy)-2-fluorophenyl)-3-imino-7-(methoxymethyl)-2-methyloctahydropyrano[3,4-e][1,2,4]thiadiazine 1,1-dioxide

| 13 | 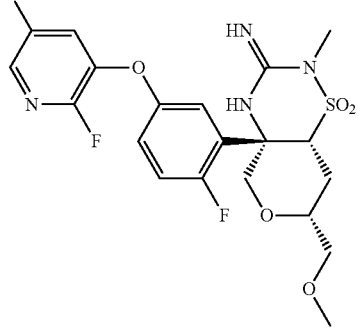 | 487.1 | 2.1 | 10 |

δ (400 MHz, CDCl₃): 1.81-1.66 (1 H, m), 2.25 (1 H, dd, J = 2.7, 13.3 Hz), 3.22 (3 H, s), 3.40 (3 H, s), 3.50-3.46 (1 H, m), 3.58-3.53 (1 H, m), 3.84-3.78 (1 H, m), 4.03-3.94 (2 H, m), 4.48 (1 H, td, J = 4.2, 12.3 Hz), 7.07-6.97 (2 H, m), 7.16-7.07 (1 H, m), 7.19 (1 H, dd, J = 2.7, 6.3 Hz), 7.73 (1 H, br. s.).
(4aS,7R,8aR)-4a-(5-((2,5-difluoropyridin-3-yl)oxy)-2-fluorophenyl)-3-imino-7-(methoxymethyl)-2-methyloctahydropyrano[3,4-e][1,2,4]thiadiazine 1,1-dioxide Method I

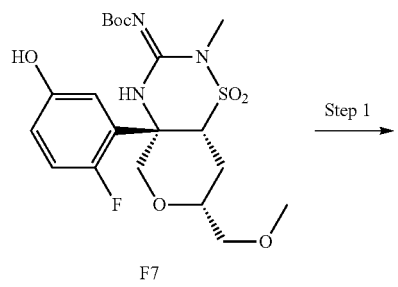 Step 1 →

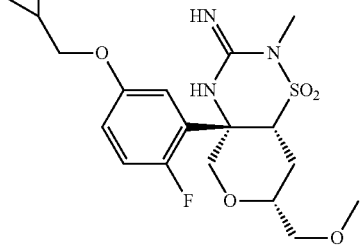

Ex 14

Step 1

A mixture of F7 (25 mg, 0.053 mmol), (bromomethyl)cyclopropane (8.6 mg, 0.063 mmol) and K₂CO₃ (22 mg, 0.16 mmol) in DMF (0.5 mL) was stirred at 40° C. for 5 h. The mixture was diluted with water (30 mL) and extracted with EtOAc (3×25 mL). The organic layer was dried over Na₂SO₄ and filtered to afford crude I1, which was used in the next step directly without further purification. MS for I1 m/e=528.2 (M+1).

Step 2

TFA (500 mg, 4.4 mmol) was added to a solution of I1 (25 mg, 0.047 mmol) in DCM (2.5 mL). The mixture was stirred at 25° C. for 0.5 h, then concentrated and purified by p-HPLC (TFA) to afford Example 14.

Example 15 was prepared in an analogous manner using Method I replacing (bromomethyl)cyclopropane with reagent L1 in step 1.

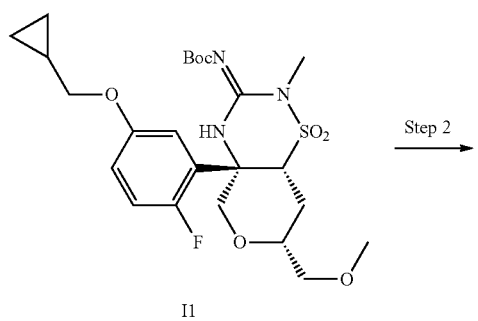 Step 2 →

I1

| Ex | Structure | LCMS m/z (M + 1) | BACE-1 $K_i$ (nM) | BACE-2 $K_i$ (nM) |
|---|---|---|---|---|
| | HNMR | | | |
| | IUPAC Name | | | |
| 14 | 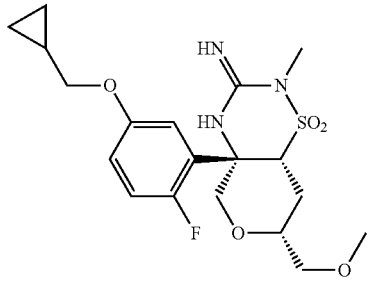 | 428.1 | 7.9 | 2.0 |

δ (400 MHz, CDCl$_3$): 0.33 (2 H, d, J = 4.9 Hz), 0.62 (2 H, d, J = 7.7 Hz), 1.24 (1 H, d, J = 7.3 Hz), 1.86-1.70 (1 H, m), 2.36 (1 H, d, J = 9.9 Hz), 3.33 (3 H, s), 3.42 (3 H, s), 3.53-3.46 (1 H, m), 3.64-3.56 (1 H, m), 3.92-3.67 (4 H, m), 4.18 (1 H, d, J = 12.8 Hz), 4.77-4.68 (1 H, m), 6.92-6.80 (2 H, m), 7.01 (1 H, dd, J = 8.9, 11.8 Hz).

(4aS,7R,8aR)-4a-(5-(cyclopropylmethoxy)-2-fluorophenyl)-3-imino-7-(methoxymethyl)-2-methyloctahydropyrano[3,4-e][1,2,4]thiadiazine 1,1-dioxide

| 15 | 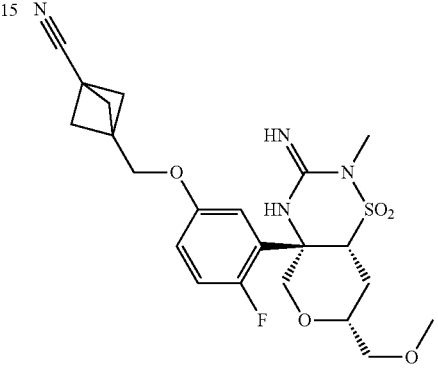 | 479.1 | 9.1 | 28 |

δ (400 MHz, CDCl$_3$): 1.80-1.74 (1 H, m), 2.28 (6 H, s), 2.37 (1 H, dd, J = 3.3, 13.5 Hz), 3.33 (3 H, s), 3.42 (3 H, s), 3.54-3.46 (1 H, m), 3.65-3.56 (1 H, m), 3.95-3.77 (4 H, m), 4.23-4.07 (1 H, m), 4.76 (1 H, td, J = 5.7, 12.1 Hz), 6.91-6.75 (2 H, m), 7.02 (1 H, dd, J = 9.0, 11.7 Hz).

3-((4-fluoro-3-((4aS,7R,8aR)-3-imino-7-(methoxymethyl)-2-methyl-1,1-dioxidooctahydropyrano[3,4-e][1,2,4]thiadiazin-4a-yl)phenoxy)methyl)bicyclo[1.1.1]pentane-1-carbonitrile Method J

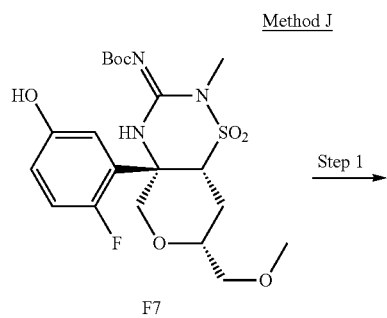

F7

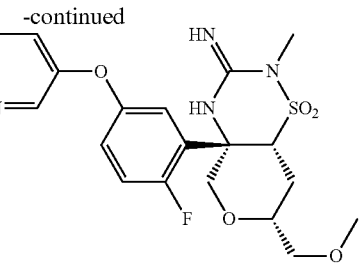

Ex 16

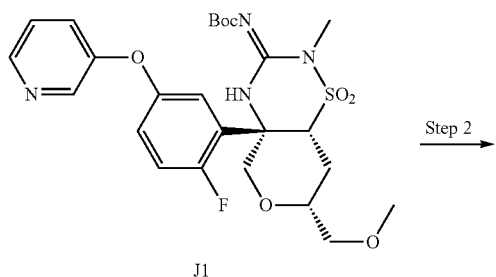

J1

Step 1

A flask was charged with F7 (15 mg, 0.032 mmol), copper (II) acetate (12 mg, 0.063 mmol), pyridin-3-ylboronic acid (12 mg, 0.095 mmol) and 4A molecular sieves (200 mg). The mixture was diluted with DCM (0.5 mL), followed by the addition of $Et_3N$ (0.022 mL, 0.16 mmol), and the resulting reaction mixture was stirred at 25° C. for 4 days under $O_2$. The mixture was diluted with water (20 mL) and extracted with EtOAc (4×15 mL). The combined organic layers were washed with brine (10 mL), dried over $Na_2SO_4$, filtered and concentrated. The resulting residue was purified by p-HPLC (TFA) to afford J1. MS for J1 m/e=551.2 (M+1).

Step 2

Hydrogen chloride (5.0 mL, 20 mmol) (4 M in EtOAc) was added to J1 (11 mg, 0.020 mmol) and the mixture was stirred at 25° C. for 2 h, then concentrated to afford Example 16.

Example 17 was prepared in an analogous manner using Method J replacing pyridin-3-ylboronic acid with the appropriate reagent in step 1.

| Ex | Structure / IUPAC Name / HNMR | LCMS m/z (M + 1) | BACE-1 $K_i$ (nM) | BACE-2 $K_i$ (nM) |
|---|---|---|---|---|
| 16 | (400 MHz, MeOH-d): 1.83-1.73 (1 H, m), 2.26-2.17 (1 H, m), 3.18 (3 H, s), 3.30 (3 H, s), 3.51-3.41 (2 H, m), 3.88-3.79 (1 H, m), 4.03-3.92 (2 H, m), 5.04 (1 H, d, J = 11.7 Hz), 7.32-7.19 (3 H, m), 7.78-7.70 (1 H, m), 7.87-7.78 (1 H, m), 8.40 (2 H, br. s.).<br>(4aS,7R,8aR)-4a-(2-fluoro-5-(pyridin-3-yloxy)phenyl)-3-imino-7-(methoxymethyl)-2-methyloctahydropyrano[3,4-e][1,2,4]thiadiazine 1,1-dioxide | 451.1 | 39 | 52 |

| | | | | |
|---|---|---|---|---|
| 17 | 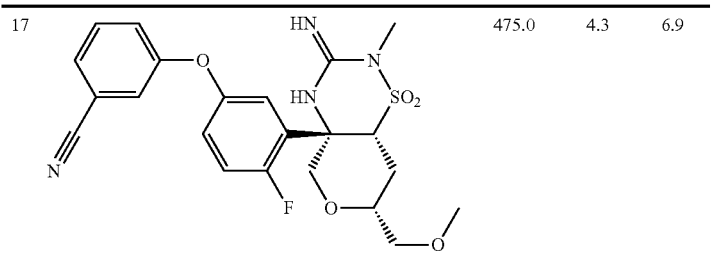 | 475.0 | 4.3 | 6.9 |

(400 MHz, MeOH-d): 1.88 (1 H, q, J = 12.1 Hz), 2.29 (1 H, dd, J = 2.7, 13.7 Hz), 3.25 (3 H, s), 3.38 (3 H, s), 3.61-3.47 (2 H, m), 3.95-3.85 (1 H, m), 4.10-3.98 (2 H, m), 5.09 (1 H, td, J = 4.0, 8.1 Hz), 7.06 (1 H, br. s.), 7.19-7.11 (1 H, m), 7.35-7.20 (3 H, m), 7.48-7.42 (1 H, m), 7.56-7.49 (1 H, m).
3-(4-fluoro-3-((4aS,7R,8aR)-3-imino-7-(methoxymethyl)-2-methyl-1,1-dioxidooctahydropyrano[3,4-e][1,2,4]thiadiazin-4a-yl)phenoxy)benzonitrile Method K

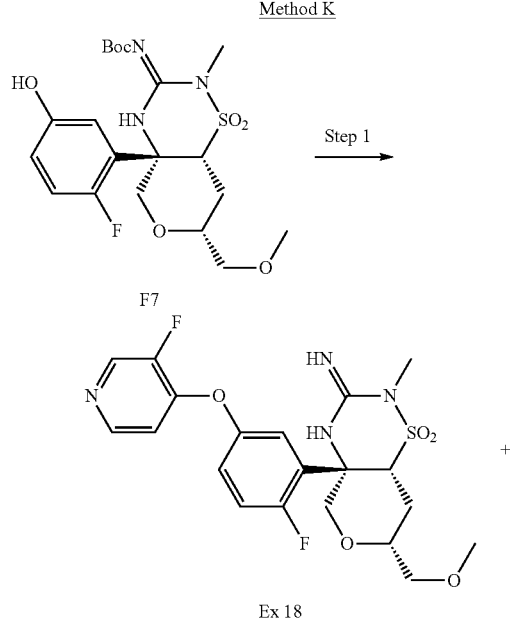

Step 1

To a solution of F7 (25 mg, 0.053 mmol) and 4-chloro-3-fluoropyridine (21 mg, 0.16 mmol) in DMA (0.3 mL) was added $K_2CO_3$ (15 mg, 0.11 mmol) and the mixture was stirred at 100° C. for 2 h. The reaction mixture was diluted with water (25 mL) and extracted with EtOAc (3×10 mL). The combined organic layers were washed with brine (10 mL), dried over $Na_2SO_4$, filtered and concentrated. The resulting residue was purified by p-HPLC (TFA) to afford Example 18 and Example 19.

| Ex | Structure | LCMS m/z (M + 1) | BACE-1 $K_i$ (nM) | BACE-2 $K_i$ (nM) |
|---|---|---|---|---|
| | HNMR | | | |
| | IUPAC Name | | | |
| 18 | 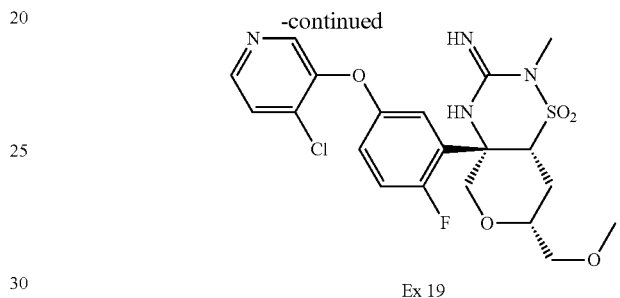 | 469.0 | 28 | 36 |

δ (400 MHz, MeOH-d): 1.95-1.81 (1 H, m), 2.36-2.26 (1 H, m), 3.25 (3 H, s), 3.38 (3 H, s), 3.61-3.48 (2 H, m), 3.97-3.86 (1 H, m), 4.05 (2 H, br. s.), 5.16-5.05 (1 H, m), 6.88 (1 H, t, J = 6.5 Hz), 7.42-7.19 (3 H, m), 8.27 (1 H, d, J = 5.5 Hz), 8.57 (1 H, d, J = 3.1 Hz).

| | | | | |
|---|---|---|---|---|
| | (4aS,7R,8aR)-4a-(2-fluoro-5-((3-fluoropyridin-4-yl)oxy)phenyl)-3-imino-7-<br>(methoxymethyl)-2-methyloctahydropyrano[3,4-e][1,2,4]thiadiazine 1,1-dioxide | | | |
| 19 | 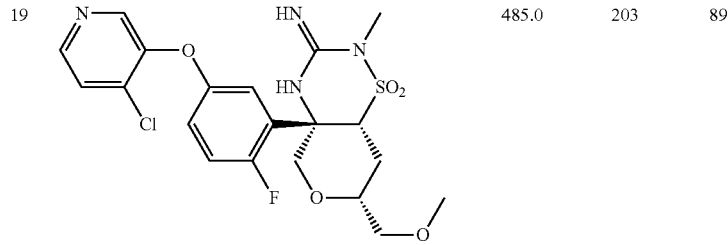 | 485.0 | 203 | 89 |
| | δ (400 MHz, MeOH-d): 1.91 (1 H, q, J = 12.3 Hz), 2.35-2.24 (1 H, m), 3.26 (3 H, s), 3.40<br>(3 H, s), 3.58-3.52 (2 H, m), 3.96-3.90 (1 H, m), 4.09-3.99 (2 H, m), 5.15-5.08 (1 H, m),<br>7.03 (1 H, br. s.), 7.17-7.09 (1 H, m), 7.30 (1 H, dd, J = 9.0, 11.7 Hz), 7.65 (1 H, d,<br>J = 5.1 Hz), 8.20 (1 H, s), 8.34 (1 H, d, J = 5.1 Hz).<br>(4aS,7R,8aR)-4a-(5-((4-chloropyridin-3-yl)oxy)-2-fluorophenyl)-3-imino-7-<br>(methoxymethyl)-2-methyloctahydropyrano[3,4-e][1,2,4]thiadiazine 1,1-dioxide | | | |

Method L

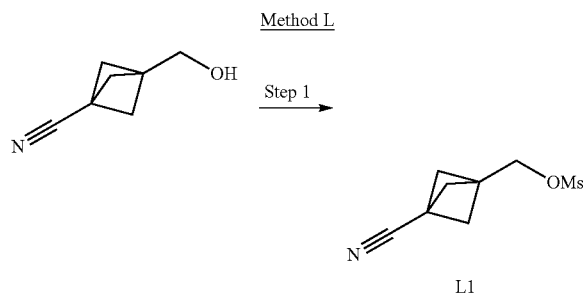

Step 1

To a solution of 3-(hydroxymethyl)bicyclo[1.1.1]pentane-1-carbonitrile (1.0 g, 8.1 mmol) in DCM (10 mL) at 0° C. was added methanesulfonyl chloride (0.76 mL, 9.7 mmol) followed by TEA (1.6 mL, 11 mmol). The reaction was stirred at 0° C. for 1 h, then the mixture was partitioned between DCM and water. The organic layer was washed with brine, dried with MgSO$_4$, concentrated to afford L1.

Assays

Protocols used to determine the recited potency values for the compounds of the invention are described below.

BACE1 HTRF FRET Assay

Reagents: Na$^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3x the final desired concentration in a volume of 10 ul are preincubated with purified human BACE1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor IC$_{50}$ values are derived from non-linear regression analysis of concentration response curves. K$_i$ values are then calculated from IC$_{50}$ values using the Cheng-Prusoff equation using a previously determined m value of 8 M for the QSY7-APP$^{swe}$-Eu substrate at BACE1. Observed K$_i$ values for the non-limiting examples are reported in the tables above.

BACE-2 Assay

Inhibitor IC$_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3x the desired final concentration in 1xBACE assay buffer (20 mM sodium acetate pH 5.0, 10% glycerol, 0.1% Brij-35) supplemented with 7.5% DMSO are preincubated with an equal volume of autoBACE-2 enzyme diluted in 1xBACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, K$_m$=8 µM for 4 µM for autoBACE-2) prepared in 1xBACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 s delay on a RUBYstar HTRF plate reader (BMG Labtechnologies). Raw RFU data is normalized to maximum (1.0 nM BACE/DMSO) and minimum (no enzyme/DMSO) RFU values. IC$_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation. Observed $K_i$ values for the non-limiting examples are reported in the tables above.

What is claimed is:

1. A compound, or a pharmaceutically acceptable salt thereof, said compound having the structural Formula (I):

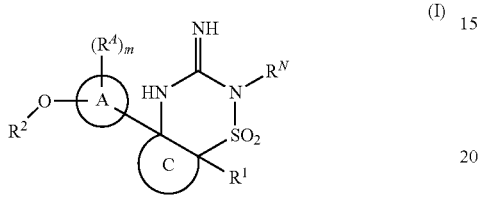

or a tautomer thereof having the structural Formula (I'):

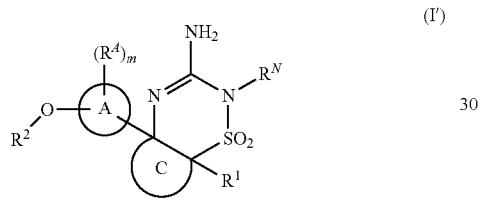

or pharmaceutically acceptable salt thereof, wherein:

ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group, wherein $R^{C1}$ and $R^{C2}$ are each independently selected from the group consisting of H, halogen, —C(O)O—($C_1$-$C_6$-alkyl), alkyl, cycloalkyl, -alkyl-cycloalkyl, -heterocycloalkyl, -alkyl-heterocycloalkyl, aryl, -alkyl-aryl, heteroaryl, and -alkyl-heteroaryl, wherein each said alkyl, cycloalkyl, heterocycloalkyl, aryl, and heteroaryl of $R^{C1}$ and $R^{C2}$ are optionally substituted with one or more $R^3$, and wherein 1 to 2 non-adjacent, non-terminal carbon atoms in each said alkyl of $R^{C1}$ and $R^{C2}$ are optionally independently replaced with —O—, —NH—, —N($C_1$-$C_6$-alkyl)-, —S—, —S(O)—, or —S(O)$_2$—, or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms, wherein 1 of said carbon atoms may be replaced with —O—, —NH—, —N($C_1$-$C_6$-alkyl)-, —N($C_1$-$C_6$-haloalkyl)-, —S—, —S(O)—, or —S(O)$_2$—, and wherein 1 to 2 of the carbon atoms of said spirocyclic ring may be optionally independently substituted with 1 to 2 fluorine, $C_1$-$C_6$-alkyl, $C_1$-$C_6$-haloalkyl, or —CH$_2$O—($C_1$-$C_6$-alkyl);

$R^N$ is selected from the group consisting of H, alkyl, cycloalkyl, and -alkyl-cycloalkyl, wherein each said alkyl and cycloalkyl are optionally substituted with one or more fluorine, and wherein 1 to 2 non-adjacent, non-terminal carbon atoms in each said alkyl are optionally independently replaced with —O—, —NH—, —N($C_1$-$C_6$-alkyl)-, —S—, —S(O)—, or —S(O)$_2$—;

$R^1$ is selected from the group consisting of H, halogen, and alkyl, wherein said alkyl is optionally substituted with one or more fluorine, and wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;

ring A is selected from the group consisting of aryl and heteroaryl;

m is 0 or more, provided that the value of m does not exceed the number of available substitutable hydrogen atoms on ring A;

each $R^A$ (when present) is independently selected from the group consisting of halogen, oxo, —OH, —CN, alkyl, and cycloalkyl, wherein said alkyl, and cycloalkyl of $R^A$ are each optionally independently unsubstituted or substituted with one or more fluorine, and wherein 1 to 2 non-adjacent, non-terminal carbon atoms in said alkyl are optionally independently replaced with —O—, —NH—, —N($C_1$-$C_6$-alkyl)-, —S—, —S(O)—, or —S(O)$_2$—;

$R^2$ is -alkyl-cycloalkyl, wherein said alkyl is optionally substituted with one or more fluorine, and wherein said cycloalkyl is optionally substituted with one or two groups independently selected from $R^3$, or alternatively $R^2$ is a moiety having the formula

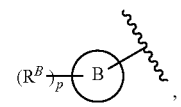

wherein ring B is selected from the group consisting of aryl, heteroaryl, cycloalkyl, and heterocycloalkyl;

p is 0 or more, provided that the value of p does not exceed the number of available substitutable hydrogen atoms on ring B; and each $R^B$ (when present) is independently selected from the group consisting of halogen, oxo, —OH, —CN, —SF$_5$, —OSF$_5$, —OR$^{2B}$, —SR$^{2B}$, alkyl, alkenyl, alkynyl, cycloalkyl, -alkyl-cycloalkyl, heterocycloalkyl, -alkyl-heterocycloalkyl, aryl, and heteroaryl, wherein each said alkyl, alkenyl, alkynyl, cycloalkyl, heterocycloalkyl, aryl, and heteroaryl of $R^B$ are each optionally independently unsubstituted or substituted with one or more groups independently selected from $R^3$, and wherein 1 to 2 non-adjacent, non-terminal carbon atoms in each said alkyl are optionally independently replaced with —O—, —NH—, —N($C_1$-$C_6$-alkyl)-, —S—, —S(O)—, or —S(O)$_2$—;

each $R^{2B}$ is independently selected from the group consisting of H, alkyl, alkenyl, alkynyl, cycloalkyl, -alkyl-cycloalkyl, heterocycloalkyl, and -alkyl-heterocycloalkyl, wherein each said alkyl, alkenyl, alkynyl, cycloalkyl, and heterocycloalkyl of $R^{2B}$ is unsubstituted or optionally substituted with one or more fluorine, and wherein 1 to 2 non-adjacent, non-terminal carbon atoms in each said alkyl are optionally independently replaced with —O—, —NH—, —N(alkyl)-, —S—, —S(O)—, or —S(O)$_2$—; and each $R^3$ (when present) is independently selected from the group consisting of halogen, —OH, —CN, $C_1$-$C_6$-alkyl, $C_2$-$C_6$-alkenyl, $C_2$-$C_6$-alkynyl, —($C_1$-$C_6$-alkyl)-OH, —O—($C_1$-$C_6$-alkyl), $C_3$-$C_6$-cycloalkyl, —($C_1$-$C_6$-alkyl)-($C_3$-$C_6$-cycloalkyl), —O—($C_3$-$C_6$-cycloalkyl), —O—($C_1$-$C_6$-alkyl)-($C_3$-$C_6$-cycloalkyl), $C_4$-$C_6$-heterocycloalkyl, —($C_1$-$C_6$-alkyl)-($C_4$-$C_6$-heterocycloalkyl), —O—($C_4$-$C_6$-heterocycloalkyl), —O—($C_1$-$C_6$-alkyl)-($C_4$-$C_6$-heterocycloalkyl), —NH$_2$, —NH—($C_1$-$C_6$-alkyl), and —N—($C_1$-$C_6$-alkyl)$_2$, wherein each said $C_1$-$C_6$-alkyl, $C_3$-$C_6$-cycloalkyl, and $C_4$-$C_6$-heterocycloalkyl are optionally substituted with one or more halogen, and wherein 1 to 2 non-adjacent, non-terminal carbon atoms in each said $C_1$-$C_6$-alkyl are optionally independently replaced with —O—, —NH—, —N—($C_1$-$C_6$-alkyl)-, —S—, —S(O)—, or —S(O)$_2$—.

2. A compound of claim 1, or a tautomer thereof, or a pharmaceutically acceptable salt of said compound or said tautomer, wherein:

$R^N$ is selected from the group consisting of H, methyl, ethyl, cyclopropyl, —CH$_2$-cyclopropyl, and —CH$_2$CH$_2$OCH$_3$, wherein each said methyl, ethyl, cyclopropyl, —CH$_2$-cyclopropyl, and —CH$_2$CH$_2$OCH$_3$ is each optionally substituted with from 1 to 3 fluorine.

3. A compound of claim 1, or a tautomer thereof, or a pharmaceutically acceptable salt of said compound or said tautomer, wherein:

ring C is selected from the group consisting of

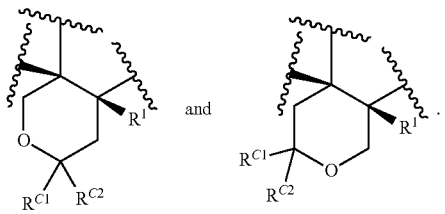

4. A compound according to claim 1, or a tautomer thereof, or a pharmaceutically acceptable salt of said compound or said tautomer, wherein:

ring C is

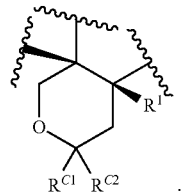

5. A compound according to claim 1, or a tautomer thereof, or a pharmaceutically acceptable salt of said compound or said tautomer, wherein:

ring A is selected from the group consisting of phenyl, pyridazinyl, pyridinyl, pyrimidinyl, pyrazinyl, pyrazolyl, triazinyl, thiazolyl, and thienyl;

m is 0, 1, 2, or 3; provided that the value of m does not exceed the number of available substitutable hydrogen atoms on ring A; and each $R^A$ (when present) is independently selected from the group consisting of fluoro, chloro, bromo, —CN, methyl, ethyl, cyclopropyl, —CH$_2$OCH$_3$, —CF$_3$, —CHF$_2$, —CH$_2$F, —OCH$_3$, —OCF$_3$, and —OCHF$_2$.

6. A compound of claim 5, or a tautomer thereof, or a pharmaceutically acceptable salt of said compound or said tautomer, wherein:

$R^2$ is a moiety having the formula

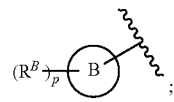

ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

p is 0, 1, 2, or 3, provided that the value of p does not exceed the number of available substitutable hydrogen atoms on ring B; and each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridinyl, oxadiazolyl, isoxazolyl, oxazolyl, pyrazolyl, pyrrolyl, and triazolyl, wherein each said phenyl, pyridinyl, oxadiazolyl, isoxazolyl, oxazolyl, pyrazolyl, pyrrolyl, and triazolyl is optionally substituted with from 1 to 3 substituents independently selected from the group consisting of fluoro, chloro, —CN, methyl, —OCH$_3$, and —CF$_3$.

7. A compound of claim 5, or a tautomer thereof, or a pharmaceutically acceptable salt of said compound or said tautomer, wherein:

$R^2$ is —($C_1$-$C_3$-alkyl)-($C_3$-$C_6$-cycloalkyl), wherein said $C_1$-$C_3$ alkyl is optionally substituted with one or more fluorine, provided that the number of fluorine atoms does not exceed the number of available substitutable hydrogen atoms on said C1-C3 alkyl group, and wherein said $C_3$-$C_6$ cycloalkyl is optionally substituted with one or two groups independently selected from the group consisting of fluoro, chloro, —CN, methyl, ethyl, —CH₂F, —CHF₂, —CF₃, —CF₂CH₃, —CH₂OCH₃,
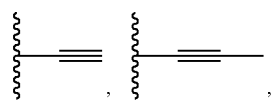
—CH₂H, —OMe, —OCH₂F, —OCHF₂, —OCF₃, —NH₂, —NHCH₃, —N(CH₃)₂, —CH₂NH₂, —CH₂NHCH₃, and —CH₂N(CH₃).
8. A compound of claim 1, or a tautomer thereof, or a pharmaceutically acceptable salt of said compound or said tautomer, said compound selected from the group consisting of:
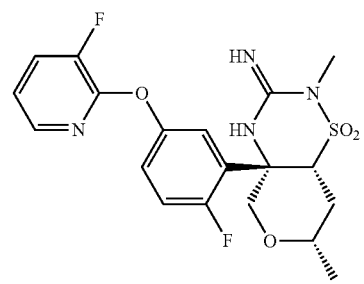 [SMILES: C[C@H]1C[C@@H]2[C@](c3cc(Oc4ncccc4F)ccc3F)(CO1)NC(=N)N(C)S2(=O)=O]
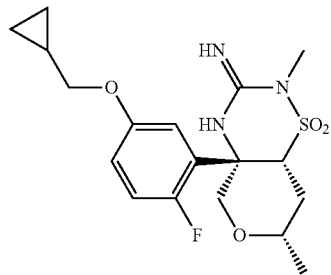
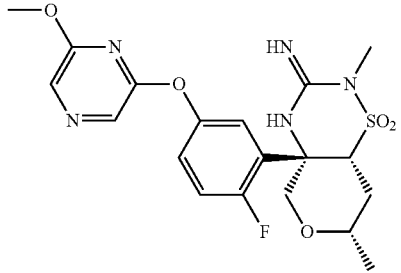 [SMILES: COc1ccnc(Oc2ccc(F)c([C@]34CO[C@@H](C)C[C@H]3S(=O)(=O)N(C)C(=N)N4)c2)n1]
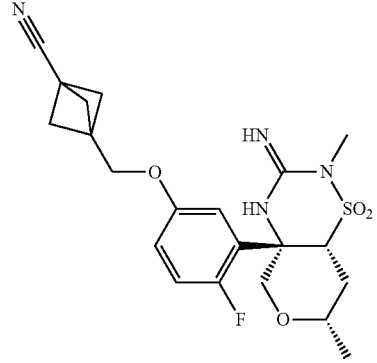
-continued
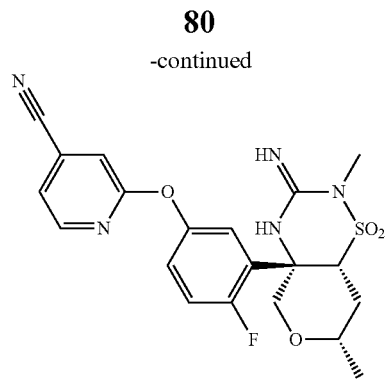
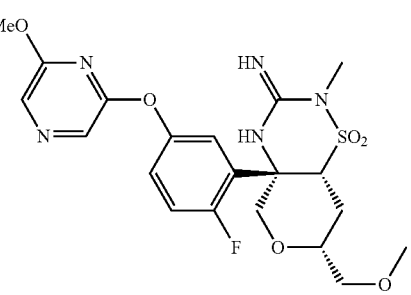
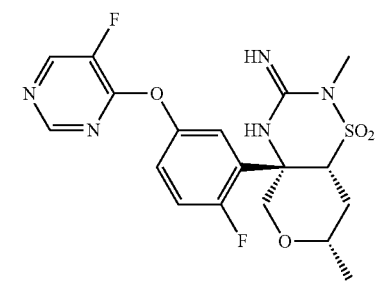 [SMILES: C[C@H]1C[C@@H]2[C@](c3cc(Oc4ncncc4F)ccc3F)(CO1)NC(=N)N(C)S2(=O)=O]
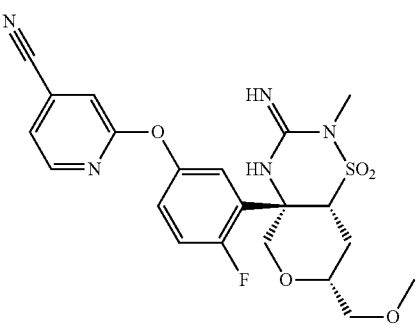
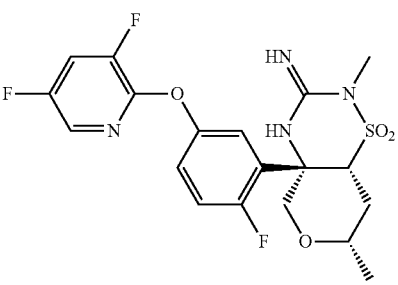 [SMILES: C[C@H]1C[C@@H]2[C@](c3cc(Oc4ncc(F)cc4F)ccc3F)(CO1)NC(=N)N(C)S2(=O)=O]

81
-continued

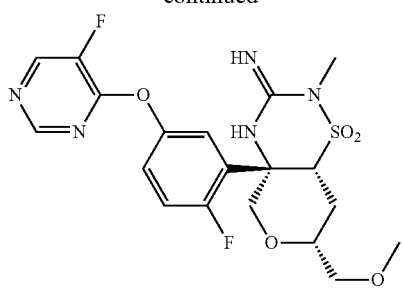

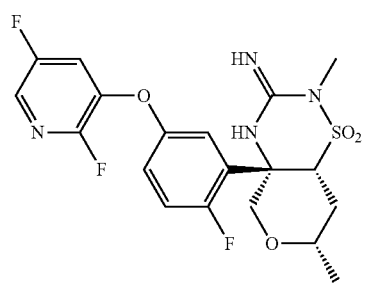 [SMILES: C[C@H]1C[C@@H]2[C@](c3cc(Oc4cc(F)cnc4F)ccc3F)(CO1)NC(=N)N(C)S2(=O)=O]

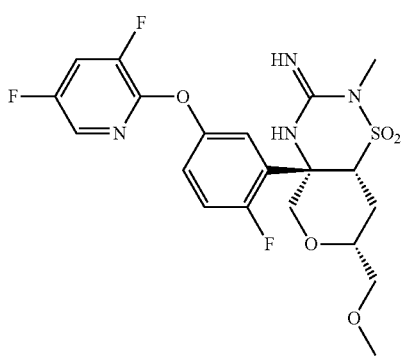 [SMILES: COC[C@H]1C[C@@H]2[C@](c3cc(Oc4ncc(F)cc4F)ccc3F)(CO1)NC(=N)N(C)S2(=O)=O]

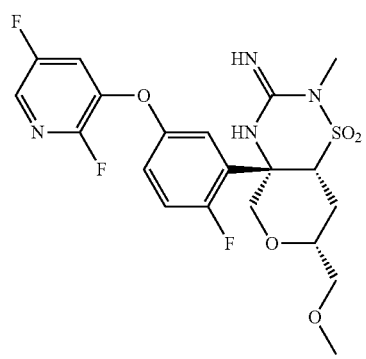 [SMILES: COC[C@H]1C[C@@H]2[C@](c3cc(Oc4cc(F)cnc4F)ccc3F)(CO1)NC(=N)N(C)S2(=O)=O]

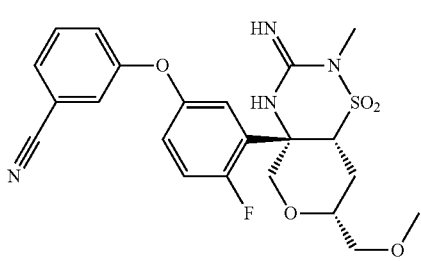 [SMILES: COC[C@H]1C[C@@H]2[C@](c3cc(Oc4cccc(C#N)c4)ccc3F)(CO1)NC(=N)N(C)S2(=O)=O]

82
-continued

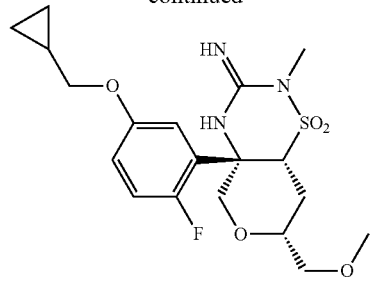

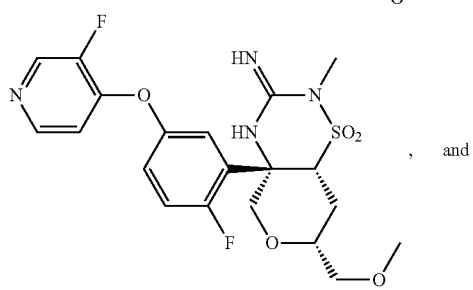

, and

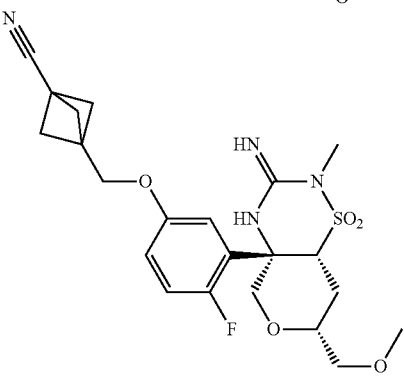

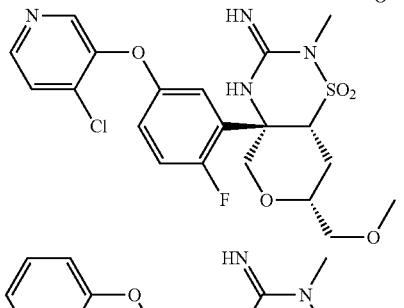

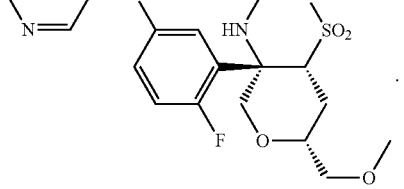

9. A pharmaceutical composition comprising a compound according to claim 1, or a tautomer thereof, or a pharmaceutically acceptable salt of said compound or said tautomer, and a pharmaceutically acceptable carrier or diluent.

10. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim 1, or a tautomer thereof, or a pharmaceutically acceptable salt of said compound or said tautomer, to a patient in need thereof in an amount effective to treat said disease or pathology.

11. The method of claim 10, wherein said disease or pathology is Alzheimer's disease.

* * * * *